United States Patent
Ballatore et al.

(10) Patent No.: US 9,643,919 B2
(45) Date of Patent: May 9, 2017

(54) CYCLOALKYL-DIONE DERIVATIVES AND METHODS OF THEIR USE

(71) Applicant: The Trustees of The University of Pennsylvania, Philadelphia, PA (US)

(72) Inventors: Carlo Ballatore, Philadelphia, PA (US); Kurt R. Brunden, Media, PA (US); Virginia M. Y. Lee, Philadelphia, PA (US); Amos B. Smith, III, Merion, PA (US); John Q. Trojanowski, Philadelphia, PA (US); Xiaozhao Wang, Drexel Hill, PA (US)

(73) Assignee: The Trustees Of The University Of Pennsylvania, Philadelphia, PA (US)

(*) Notice: Subject to any disclaimer, the term of this patent is extended or adjusted under 35 U.S.C. 154(b) by 0 days.

(21) Appl. No.: 14/781,424

(22) PCT Filed: Apr. 3, 2014

(86) PCT No.: PCT/US2014/032742
§ 371 (c)(1),
(2) Date: Sep. 30, 2015

(87) PCT Pub. No.: WO2014/165633
PCT Pub. Date: Oct. 9, 2014

(65) Prior Publication Data
US 2016/0031805 A1  Feb. 4, 2016

Related U.S. Application Data

(60) Provisional application No. 61/808,260, filed on Apr. 4, 2013.

(51) Int. Cl.
*C07C 311/20* (2006.01)

(52) U.S. Cl.
CPC ........ *C07C 311/20* (2013.01); *C07C 2101/10* (2013.01); *C07C 2102/10* (2013.01)

(58) Field of Classification Search
CPC  C07C 311/20; C07C 2101/10; C07C 2102/10
See application file for complete search history.

(56) References Cited

U.S. PATENT DOCUMENTS

| | | | |
|---|---|---|---|
| 4,921,998 A | 5/1990 | Niewohner et al. | |
| 5,472,979 A | 12/1995 | Lavielle et al. | |
| 2012/0329877 A1 | 12/2012 | Atasoylu et al. | |

FOREIGN PATENT DOCUMENTS

WO  WO 2012/015944 A2  2/2012

OTHER PUBLICATIONS

Ballatore et al., "Cyclopentane-1, 3-dione: A Novel Isostere for the Carboxylic Acid Functional Group. Application to the Design of Potent Thromboxane (A2) Receptor Antagonists", J. Med. Chem., Oct. 2011, 54(19), 6969-6983.

Boothe et al., "Synthesis of Aureomycin Degradation Products. II", Journal of the American Chemical Society, Apr. 1953, 75(7), 1732-1733.

Dickinson et al., "Thromboxane Modulating Agents. 3. 1H-Imidazol-1-ylalkyl- and 3-Pyridinylalkyl-Substituted 3-[2-[(Arylsulfonyl)amino]ethyl]benzenepropanoic Acid Derivatives as Dual Thromboxane Synthase Inhibitor/Thromboxane Receptor Antagonists", J. Med. Chem., Oct. 1997, 40(21), 3442-3452.

Dogne et al., "From the design to the clinical application of thromboxane modulators", Current Pharmaceutical Design, Mar. 2006, 12(8), 903-923.

Dogne et al., "Thromboxane A2 Inhibition: Therapeutic Potential in Bronchial Asthma", Am. J. Respir. Med., Jan. 2002, 1(1), 11-17.

Henry et al., "Mitsunobu reactions of n-alkyl and n-acyl sulfonamides-an efficient route to protected amines", Tetrahedron Letters, 1989, 30(42), 5709-5712.

Hiraga, "Structures of cyclopentanepolyones", Chemical & Pharmaceutical Bulletin, Nov. 1965, 13(11), 1300-1306.

Katrusiak, "Structure of 2-methyl-1, 3-cyclopentanedione", Acta Crystallographica Section C: Crystal Structure Communications, 1989, C45, 1897-1899.

Katrusiak, "Structure of I, 3-cyclopentanedione", Acta Crystallographica Section C: Crystal Structure Communications, 1990, C46, 1289-1293.

(Continued)

*Primary Examiner* — Sahar Javanmard
(74) *Attorney, Agent, or Firm* — Baker & Hostetler LLP

(57) ABSTRACT

The present invention is directed to compounds of formula I: wherein A is n is 0, 1, or 2; m is 0 or 1; $R_1$ is H or $C_{1-6}$alkyl and $R_2$ is H, $C_{1-6}$alkyl, $C_{1-6}$alkaryl, aryl, or heteroaryl; and X is O or NH. Tautomers, enantiomers, and diastereomers, as well as pharmaceutically acceptable salt forms, of compounds of formula I are also within the scope of the invention. Methods of preparing and using the compounds of formula I are also described.

formula I

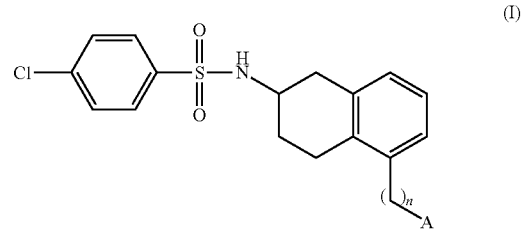

wherein A is

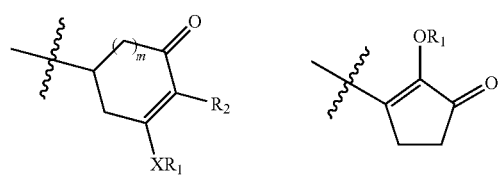

30 Claims, No Drawings

(56) References Cited

OTHER PUBLICATIONS

Koreeda et al., "Easy generation of the dianions of 3-isobutoxycyclopent-2-en-1-ones and their reactions", Journal of the Chemical Society, Chemical Communications, 1979, Issue 10, 449-450.
Nakahata, "Thromboxane A2: Physiology/pathophysiology, cellular signal transduction and pharmacology", Pharmacol. Therapeut., Apr. 2008, 118(1), 18-35.
Patani et al., "Bioisosterism: A Rational Approach in Drug Design", Chem. Rev., Dec. 1996, 96(8), 3147-3176.
Peters et al., "Noncovalent Interactions between Tetrazole and an N,N'-Diethyl-Substituted Benzamidine", The Journal of Organic Chemistry, May 2001, 66(10), 3291-3298.
Ramachary et al., "Direct amino acid-catalyzed cascade biomimetic reductive alkylations: application to the asymmetric synthesis of Hajos-Parrish ketone analogues", Organic & Biomolecular Chemistry, Nov. 2008, 6(22), 4176-4187.
Shenker et al., "The G protein coupled to the thromboxane A2 receptor in human platelets is a member of the novel Gq family", J. Biol. Chem., May 1991, 266, 9309-9313.
Shineman et al., "Thromboxane receptor activation mediates isoprostane-induced increases in amyloid pathology in Tg2576 mice", The J. of Neuroscience, Apr. 30, 2008, 28(18), 4785-4794.
Soper, et al. "Brain-Penetrant Tetrahydronaphthalene Thromboxane A-2-Prostanoid (TP) Receptor Antagonists as Prototype Therapeutics for Alzheimer's Disease", ACS Chem. Neurosci., Nov. 2012, 3(11):928-40.
Suzuki et al., "Prophylactic Effects of the Histamine H1 Receptor Antagonist Epinastine and the Dual Thromboxane A2 Receptor and Chemoattractant Receptor-Homologous Molecule Expressed on Th2 Cells Antagonist Ramatroban on Allergic Rhinitis Model in Mice", Biol. Pharm. Bull., Apr. 2011, 34(4), 507-510.
Tilley et al., "Carboxylic acids and tetrazoles as isosteric replacements for sulfate in cholecystokinin analogs", Journal of Medicinal Chemistry, Mar. 1991, 34(3), 1125-1136.
Tominey et al., "Unusually Weak Binding Interactions in Tetrazole-Amidine Complexes", Organic Letters, Mar. 2006, 8(7), 1279-1282.
Xu et al., "The Thromboxane Receptor Antagonist S18886 Attenuates Renal Oxidant Stress and Proteinuria in Diabetic Apolipoprotein E-Deficient Mice", Diabetes, Jan. 2006, 55(1),110-119.
Yamamoto et al., "Modeling of human thromboxane A2 receptor and analysis of the receptor-ligand interaction", J Med Chem., Apr. 1993, 36(7), 820-825.

CYCLOALKYL-DIONE DERIVATIVES AND METHODS OF THEIR USE

CROSS REFERENCE TO RELATED APPLICATION

This application is a National Stage Application filed under 35 U.S.C. 371 of International Application No. PCT/US2014/032742, filed Apr. 3, 2014, which claims the benefit of U.S. Provisional Application No. 61/808,260, filed Apr. 4, 2013, the entirety of which is incorporated by reference herein.

GOVERNMENT SUPPORT

This invention was made with government support under grant number NIH/NIA RO1-AG034140, awarded by the National Institutes of Health/National Institute on Aging. The government has certain rights in the invention.

TECHNICAL FIELD

The invention is directed to compounds that include cycloalkyl-dione derivatives as replacements for carboxylic acid moieties.

BACKGROUND

The carboxylic acid functional group plays a cardinal role in the biochemistry of living systems as well as in drug design. A wide variety of endogenous substances, such as amino acids, triglycerides and prostanoids possess the carboxylic acid moiety. Furthermore, this functional group is often part of the pharmacophore of diverse classes of therapeutic agents. Indeed, a large number of carboxylic acid-containing drugs (>450) have been marketed worldwide, including widely used non-steroidal anti-inflammatory agents, antibiotics, anti-coagulants, and cholesterol-lowering statins, among others. The acidity, combined with the ability to establish relatively strong electrostatic interactions and H-bonds, are the reasons this functional group is often a key determinant in drug-target interactions. However, despite the success of carboxylic acid drugs, the presence of a carboxylic acid residue in a drug or a drug candidate can represent a liability. For instance, a reduced ability to passively diffuse across biological membranes may raise a significant challenge, particularly in the context of CNS-drug discovery, where the blood-brain barrier (BBB) can be relatively impermeable to negatively charged carboxylates. Furthermore, idiosyncratic drug toxicities arising from the metabolism of the carboxylic acid (e.g., glucuronidation) have been linked to withdrawals of marketed drugs. Thus, to avoid these and other possible shortcomings, the replacement of the carboxylic acid functional group with a suitable surrogate, or (bio)-isostere, can represent an effective strategy.

The thromboxane $A_2$ prostanoid (TP) receptor is known to be involved in platelet aggregation, as well as vaso- and broncho-constriction. Furthermore, the TP receptor signaling cascade has been implicated in the pathogenesis of Alzheimer's disease and certain forms of cancer. TP receptor antagonists can be therapeutically useful to treat conditions including cardiovascular and respiratory diseases, certain forms of cancer, and neurodegenerative diseases. As such, effective antagonists of the TP receptor are needed.

SUMMARY

The present invention is directed to compounds of formula I:

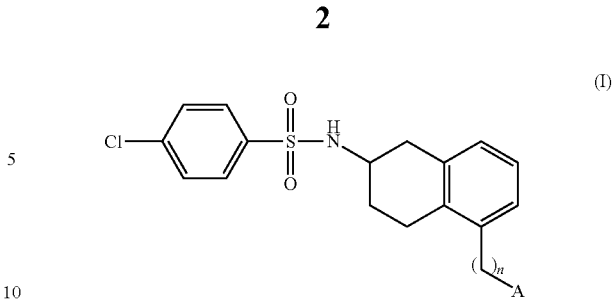

wherein A is

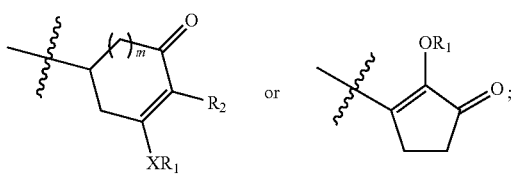

n is 0, 1, or 2; m is 0 or 1; $R_1$ is H or $C_{1-6}$alkyl and $R_2$ is H, $C_{1-6}$alkyl, $C_{1-6}$alkaryl, aryl, or heteroaryl; and X is O or NH. Tautomers, enantiomers, and diastereomers, as well as pharmaceutically acceptable salt forms, of compounds of formula I are also within the scope of the invention. Methods of preparing and using the compounds of formula I are also described.

DETAILED DESCRIPTION OF ILLUSTRATIVE EMBODIMENTS

Compound 12 is a known thromboxane-A2 prostanoid (TP) receptor antagonist:

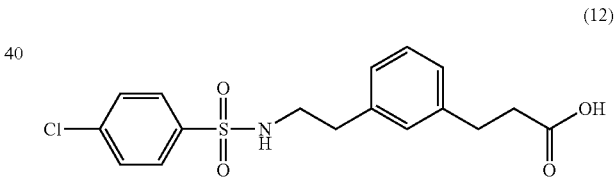

(Dickinson R. P., et al, "Thromboxane Modulating Agents. 3. 1H-Imidazol-1-ylalkyl- and 3-Pyridinylalkyl-Substituted 3-[2-[(Arylsulfonyl)amino]ethyl]benzenepropanoic Acid Derivatives as Dual Thromboxane Synthase Inhibitor/Thromboxane Receptor Antagonists," J. Med. Chem. 1997, 40(21), 3442-3452, the entirety of which is incorporated by reference). Compound 12 is useful for the treatment of thrombus in patients. In addition, thromboxane receptor antagonists like compound 12 have been shown to be useful in the treatment of Alzheimer's disease. See Shineman, D. W. et al, Thromboxane Receptor Activation Mediates Isoprostane-Induced Increases in Amyloid Pathology in Tg2576 Mice, The J. of Neuroscience, Apr. 30, 2008 28(18): 4785-4794, the entirety of which is incorporated by reference.

It has been demonstrated that the carboxylic acid moiety of Compound 12 can be replaced by cycloalkyl-1,3-dione and cycloalkyl-1,2-dione derivatives. Those compounds have commensurate biological activity, as compared to, for example, compound 12. See Ballatore, C. et al, Cyclopentane-1,3-dione: a novel isostere for the carboxylic acid functional group. Application to the design of potent thromboxane (A2) receptor antagonists, J. Med. Chem. 2011 Oct. 13:54(19):6969-83 and U.S. Published Application No. 2012/0329877, each of which is incorporated by reference herein. The compounds of the invention, which include a fused, bicyclic ring structure, not present in Compound 12 or U.S. Published Application No. 2012/0329877, demonstrate excellent biological activity.

Within the scope of the invention are compounds of formula I:

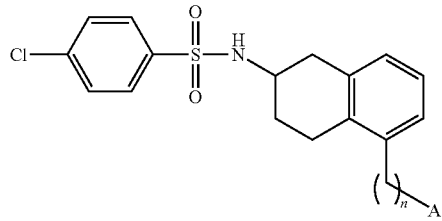

(I)

wherein
A is

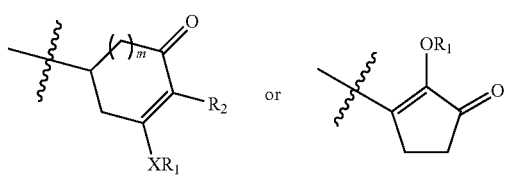

n is 0, 1, or 2;
m is 0 or 1;
$R_1$ is H or $C_{1-6}$alkyl;
$R_2$ is H, $C_{1-6}$alkyl, $C_{1-6}$alkaryl, aryl, or heteroaryl; and
X is O or NH;
or a tautomer, enantiomer, or diastereomer thereof;
or pharmaceutically acceptable salt form thereof.

In preferred embodiments, A is

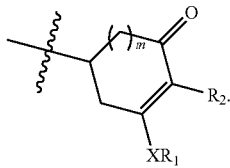

In such embodiments, m is preferably 0. It is also preferred that n is 0 or 1, with n is 1 being most preferred. Particularly preferred embodiments are those wherein m is 0 and n is 1. It is also preferred that $R_1$ is H. It is also preferred that in embodiments employing A is

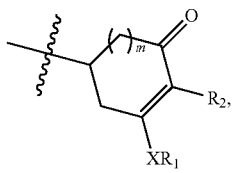

X is O.

In particularly preferred embodiments, A is

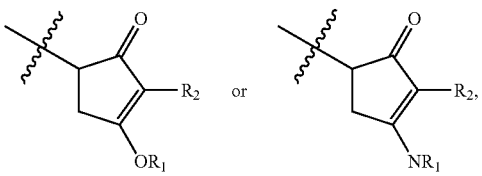

preferably

Preferably, $R_2$ is $C_{1-6}$alkyl. Particularly preferred embodiments include those wherein $R_2$ is methyl, ethyl, propyl, isopropyl, —$CH_2$-cyclopropyl, —$CH_2$-isopropyl or cyclohexyl. In other embodiments, $R_2$ is H.

In still other embodiments, $R_2$ is aryl, which can be substituted or unsubstituted. Substituted or unsubstituted phenyl is particularly preferred. In certain embodiments, the aryl is unsubstituted. In embodiments wherein the aryl is substituted, the aryl can be substituted with one, two, or three substituents, which can be the same or different. In preferred embodiments, the aryl is di-substituted. Preferred aryl substitutents include $C_{1-6}$alkyl, for example, methyl, ethyl, propyl, and the like; $C_{1-6}$alkoxy, for example, methoxy, ethoxy, propoxy, and the like; and halogen, for example, fluoro, chloro, or bromo.

In other embodiments, $R_2$ is $C_{1-6}$alkaryl, which can be substituted or unsubstituted. An exemplary $C_{1-6}$alkaryl is benzyl (—$CH_2$phenyl). In some embodiments, the aryl group of the $C_{1-6}$alkaryl moiety can be unsubstituted. In embodiments wherein the aryl group of the $C_{1-6}$alkaryl moiety is substituted, the aryl can be substituted with one, two, or three substituents, which can be the same or different. Preferred substituents include $C_{1-6}$alkyl, for example, methyl, ethyl, propyl, and the like; $C_{1-6}$alkoxy, for example, methoxy, ethoxy, propoxy, and the like; and halogen, for example, fluoro, chloro, or bromo.

In yet other embodiments, $R_2$ is heteroaryl, which can be substituted or unsubstituted. In some embodiments, the heteroaryl is unsubstituted. In embodiments wherein the heteroaryl group of the $C_{1-6}$alkaryl moiety is substituted, the aryl can be substituted with one, two, or three substituents, which can be the same or different. Preferred substitutents include $C_{1-6}$alkyl, for example, methyl, ethyl, propyl, and the like; $C_{1-6}$alkoxy, for example, methoxy, ethoxy, propoxy, and the like; and halogen, for example, fluoro, chloro, or bromo.

In certain embodiments wherein A is

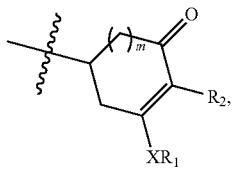

m is preferably 1. It is also preferred, in such embodiments, that n is 0 or 1, preferably 0. Particularly preferred embodiments are those wherein m is 1 and n is 0. It is also preferred that $R_1$ is H. It is also preferred that X is O.

Other embodiments include those wherein A is

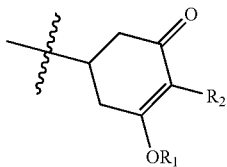

In such embodiments, $R_2$ is preferably $C_{1-6}$alkyl. Particularly preferred embodiments include those wherein $R_2$ is methyl, ethyl, propyl, isopropyl, —$CH_2$-cyclopropyl, —$CH_2$-isopropyl, or cyclohexyl. In other embodiments, $R_2$ is H.

In still other embodiments, $R_2$ is aryl, which can be substituted or unsubstituted. Substituted or unsubstituted phenyl is particularly preferred. In certain embodiments, the aryl is unsubstituted. In embodiments wherein the aryl is substituted, the aryl can be substituted with one, two, or three substituents, which can be the same or different. In preferred embodiments, the aryl is di-substituted. Preferred aryl substitutents include $C_{1-6}$alkyl, for example, methyl, ethyl, propyl, and the like; $C_{1-6}$alkoxy, for example, methoxy, ethoxy, propoxy, and the like; and halogen, for example, fluoro, chloro, or bromo.

In other embodiments, $R_2$ is $C_{1-6}$alkaryl, which can be substituted or unsubstituted. An exemplary $C_{1-6}$alkaryl is benzyl (—$CH_2$phenyl). In some embodiments, the aryl group of the $C_{1-6}$alkaryl moiety can be unsubstituted. In embodiments wherein the aryl group of the $C_{1-6}$alkaryl moiety is substituted, the aryl can be substituted with one, two, or three substituents, which can be the same or different. Preferred substituents include $C_{1-6}$alkyl, for example, methyl, ethyl, propyl, and the like; $C_{1-6}$alkoxy, for example, methoxy, ethoxy, propoxy, and the like; and halogen, for example, fluoro, chloro, or bromo.

In yet other embodiments, $R_2$ is heteroaryl, which can be substituted or unsubstituted. In some embodiments, the heteroaryl is unsubstituted. In embodiments wherein the heteroaryl group of the $C_{1-6}$alkaryl moiety is substituted, the aryl can be substituted with one, two, or three substituents, which can be the same or different. Preferred substitutents include $C_{1-6}$alkyl, for example, methyl, ethyl, propyl, and the like; $C_{1-6}$alkoxy, for example, methoxy, ethoxy, propoxy, and the like; and halogen, for example, fluoro, chloro, or bromo.

Preferred compounds of the invention are those of formula IA:

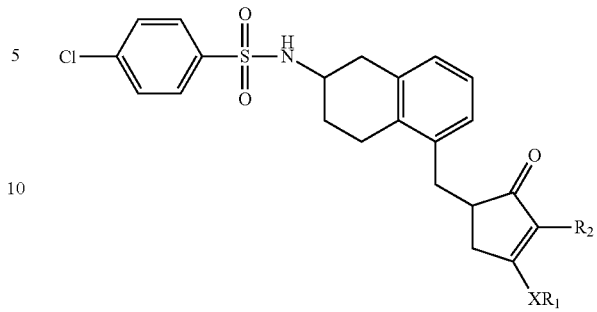

wherein
$R_1$ is H or $C_{1-6}$alkyl and
$R_2$ is H, $C_{1-6}$alkyl, $C_{1-6}$alkaryl, aryl, or heteroaryl; and
X is O or NH;
or a tautomer, enantiomer, or diastereomer thereof;
or a pharmaceutically acceptable salt form thereof.

In preferred embodiments of formula IA, X is O. In other embodiments, X is NH.

In preferred embodiments, $R_1$ is H. In other embodiments, $R_1$ is $C_{1-6}$alkyl.

In those embodiments wherein $R_1$ is H, $R_2$ is preferably H. In other embodiments wherein $R_1$ is H, $R_2$ is preferably $C_{1-6}$alkyl. In those embodiments, $R_2$ is preferably methyl, ethyl, propyl, or isopropyl. In other embodiments $R_2$ is —$CH_2$-cyclopropyl. In yet other embodiments $R_2$ is —$CH_2$-isopropyl.

In still other embodiments, $R_2$ is aryl, which can be substituted or unsubstituted. Substituted or unsubstituted phenyl is particularly preferred. In certain embodiments, the aryl is unsubstituted. In embodiments wherein the aryl is substituted, the aryl can be substituted with one, two, or three substituents, which can be the same or different. In preferred embodiments, the aryl is di-substituted. Preferred aryl substitutents include $C_{1-6}$alkyl, for example, methyl, ethyl, propyl, and the like; $C_{1-6}$alkoxy, for example, methoxy, ethoxy, propoxy, and the like; and halogen, for example, fluoro, chloro, or bromo.

In other embodiments, $R_2$ is $C_{1-6}$alkaryl, which can be substituted or unsubstituted. An exemplary $C_{1-6}$alkaryl is benzyl (—$CH_2$phenyl). In some embodiments, the aryl group of the $C_{1-6}$alkaryl moiety can be unsubstituted. In embodiments wherein the aryl group of the $C_{1-6}$alkaryl moiety is substituted, the aryl can be substituted with one, two, or three substituents, which can be the same or different. Preferred substituents include $C_{1-6}$alkyl, for example, methyl, ethyl, propyl, and the like; $C_{1-6}$alkoxy, for example, methoxy, ethoxy, propoxy, and the like; and halogen, for example, fluoro, chloro, or bromo.

In yet other embodiments, $R_2$ is heteroaryl, which can be substituted or unsubstituted. In some embodiments, the heteroaryl is unsubstituted. In embodiments wherein the heteroaryl group of the $C_{1-6}$alkaryl moiety is substituted, the aryl can be substituted with one, two, or three substituents, which can be the same or different. Preferred substitutents include $C_{1-6}$alkyl, for example, methyl, ethyl, propyl, and the like; $C_{1-6}$alkoxy, for example, methoxy, ethoxy, propoxy, and the like; and halogen, for example, fluoro, chloro, or bromo.

The pharmaceutically acceptable salt forms of compounds of formula I are also within the scope of the invention. Tautomers of compounds of formula I are also within the scope of the invention.

Pharmaceutical formulations can be prepared by combining a compound of the invention with a pharmaceutically acceptable carrier or diluent. Pharmaceutical formulations of the invention can be used to treat any disease or disorder that can be ameliorated using a TP antagonists.

As used herein, "alkyl" refers to branched or unbranched, saturated, hydrocarbons having from 1-30 carbons, preferably 1-6 carbons ($C_{1-6}$alkyl). Alkyl groups of the invention may also include one or more saturated, cyclic hydrocarbons, for example, cycloalkyl. Preferred alkyl groups include, for example, methyl, ethyl, propyl, isopropyl, butyl, sec-butyl, iso-butyl, tert-butyl, pentyl, isopentyl, hexyl, cyclopropyl, cyclobutyl, cyclohexyl, and the like.

As used herein "alkaryl" refers to a moiety including an alkylene moiety, preferably a $C_{1-6}$alkylene moiety, attached to an aryl moiety. Examples of such groups include benzyl, —$CH_2$—$CH_2$-phenyl, —$CH_2$-naphthyl, —$CH_2$—$CH_2$-naphthyl, and the like. Aryl groups of the alkaryl moieties of the invention can be unsubstituted. Alternatively, the aryl groups f the alkaryl moieties of the invention can be substituted with, for example, halogen (F, Cl, Br, I), alkyl, or alkoxy (—Oalkyl).

As used herein, "aryl" refers to an aromatic 6-10-membered carbocyclic ring, for example, phenyl and napthyl. Aryl groups used in the compounds of the invention can be unsubstituted. Alternatively, the aryl groups used in the compounds of the invention can be substituted with, for example, halogen (F, Cl, Br, I), alkyl, or alkoxy (—Oalkyl).

As used herein, "heteroaryl" refers to a mono-, di-, or tri-cyclic aromatic ring that includes at least one, preferably 1, 2, 3, or 4, heteroatoms. Heteroatoms include sulfur, oxygen, and nitrogen. Heteroaryl groups also include, for example, from 3 to about 50 carbon atoms, with 4 to 10 carbon atoms being preferred. Examples of heteroaryl groups include pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl. Heteroaryl groups of the invention can be unsubstituted. Alternatively, heteroaryl groups of the invention can be substituted with, for example, halogen (F, Cl, Br, I), alkyl, or alkoxy (—Oalkyl).

As used herein, "pharmaceutically acceptable salts" refers to those salts of compounds of the invention that are safe and effective for use in a subject and that possess the desired biological activity. Pharmaceutically acceptable salts include salts of acidic or basic groups present in compounds of the invention. Various pharmaceutically acceptable salts, ether derivatives, ester derivatives, acid derivatives, and aqueous solubility altering derivatives of the active compound also are encompassed by the present invention. The invention also includes all polymorphs and solvates, such as hydrates and those formed with organic solvents, of this compound. Such isomers, polymorphs, and solvates may be prepared by methods known in the art, such as by regiospecific and/or enantioselective synthesis and resolution, based on the disclosure provided herein.

As used herein, "therapeutically effective amount" refers to an amount effective to ameliorate or prevent the symptoms, prolong the survival of, or otherwise mitigate the undesirable effects of the disease for which the patient is being treated. Determination of a therapeutically effective amount is well within the capabilities of those skilled in the art, especially in light of the detailed disclosure provided herein.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers of the compounds of formula I are within the scope of the invention.

Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

"Tautomers" refer to compounds that are interchangeable forms of a particular compound structure, and that vary in the displacement of hydrogen atoms and electrons. Thus, two structures may be in equilibrium through the movement of $\pi$ electrons and an atom (usually H). For example, enols and ketones are tautomers because they are rapidly interconverted by treatment with either acid or base. Another example of tautomerism is the aci- and nitro-forms of phenyl nitromethane, that are likewise formed by treatment with acid or base.

Tautomeric forms may be relevant to the attainment of the optimal chemical reactivity and biological activity of a compound of interest.

The compounds of this invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

The amount of compound administered will, of course, be dependent on the subject being treated, on the subject's weight, the severity of the affliction, the manner of administration and the judgment of the prescribing physician. However, to the extent that these compounds provide improved activity relative to other known small molecules in in vivo, in vitro, and animal studies, in the broadest sense, recommended dosages are those similar to those currently prescribed for other small molecules for this same purpose.

Suitable dosage forms include but are not limited to oral, rectal, sub-lingual, mucosal, nasal, ophthalmic, subcutaneous, intramuscular, intravenous, transdermal, spinal, intrathecal, intra-articular, intra-arterial, sub-arachinoid, bronchial, lymphatic, and intra-uterille administration, and other dosage forms for systemic delivery of active ingredients. In a preferred embodiment, the dosage form is suitable for oral administration.

To prepare such pharmaceutical dosage forms, one or more of the aforementioned compounds or a pharmaceutically acceptable salt thereof, are intimately admixed with a pharmaceutical carrier according to conventional pharmaceutical compounding techniques. The carrier may take a wide variety of forms depending on the form of preparation desired for administration.

The compounds of the invention, may be administered to a subject per se or in the form of a pharmaceutical composition. Pharmaceutical compositions comprising the compounds of the invention may be manufactured by means of conventional mixing, dissolving, granulating, dragee-making, levigating, emulsifying, encapsulating, entrapping or lyophilizing processes. Pharmaceutical compositions may be formulated in a conventional manner using one or more physiologically acceptable carriers, diluents, excipients or auxiliaries which facilitate processing of the active peptides or peptide analogues into preparations which can be used pharmaceutically. Proper formulation is dependent upon the route of administration chosen.

For parenteral formulations, the carrier will usually comprise sterile water, though other ingredients, for example, ingredients that aid solubility or for preservation, may be included. Injectable solutions may also be prepared in which case appropriate stabilizing agents may be employed.

Parenteral administration may comprise any suitable form of systemic delivery or delivery directly to the CNS. Administration may for example be intravenous, intra-arterial, intrathecal, intramuscular, subcutaneous, intramuscular, intra-abdominal (e.g., intraperitoneal), etc., and may be effected by infusion pumps (external or implantable) or any other suitable means appropriate to the desired administration modality.

In preparing the compositions in oral dosage form, any of the usual pharmaceutical media may be employed. Thus, the compounds can be readily formulated by combining the compounds, salts, or analogues with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated.

The comparison compound, CNDR-51280, can be prepared according to, for example, the sequence depicted in Scheme 1.

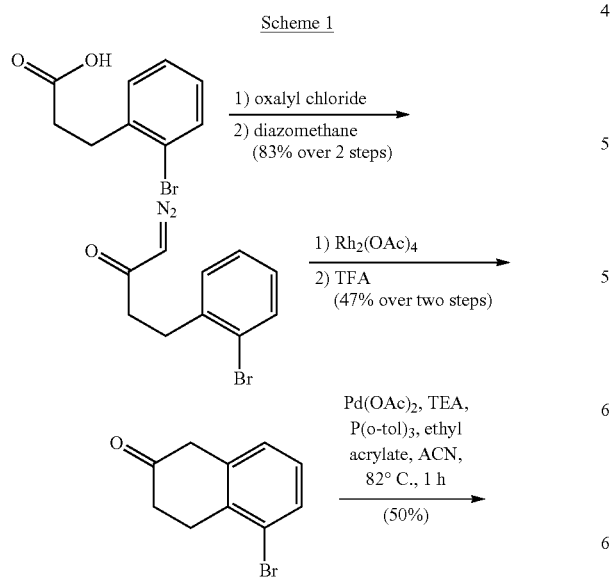

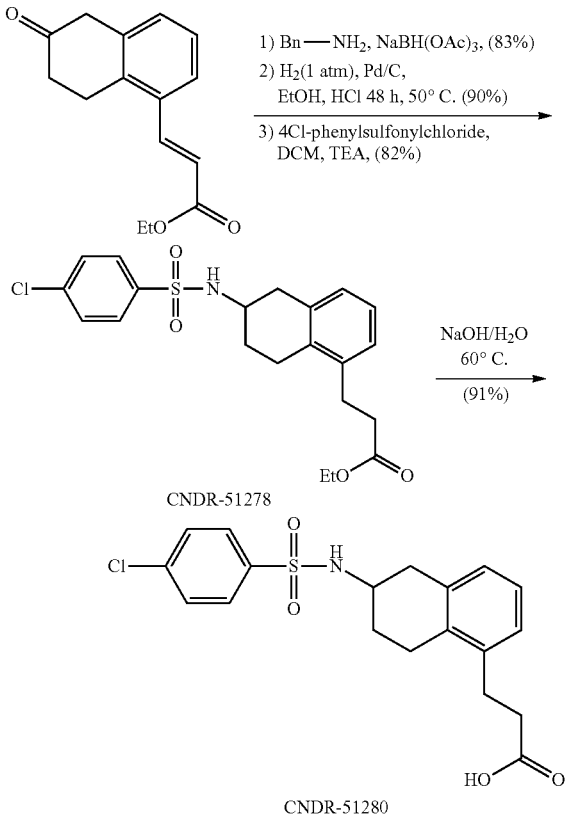

Compounds of the invention can be prepared, for example, by the sequence depicted in Scheme 2.

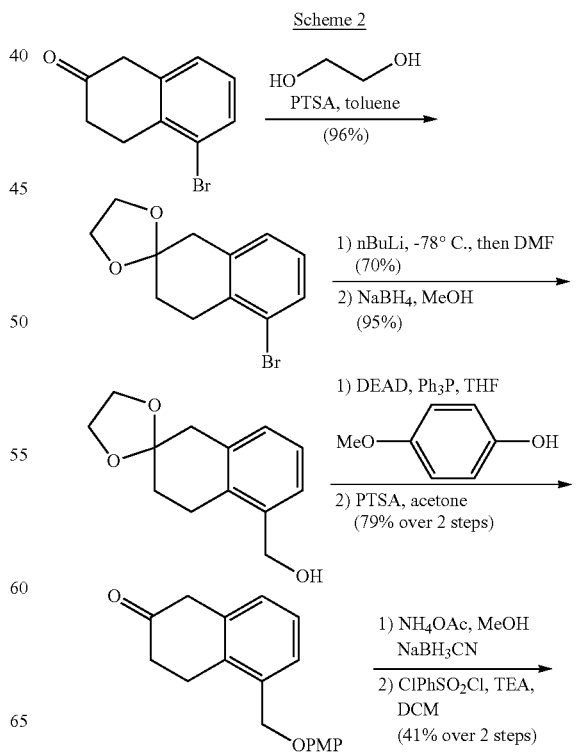

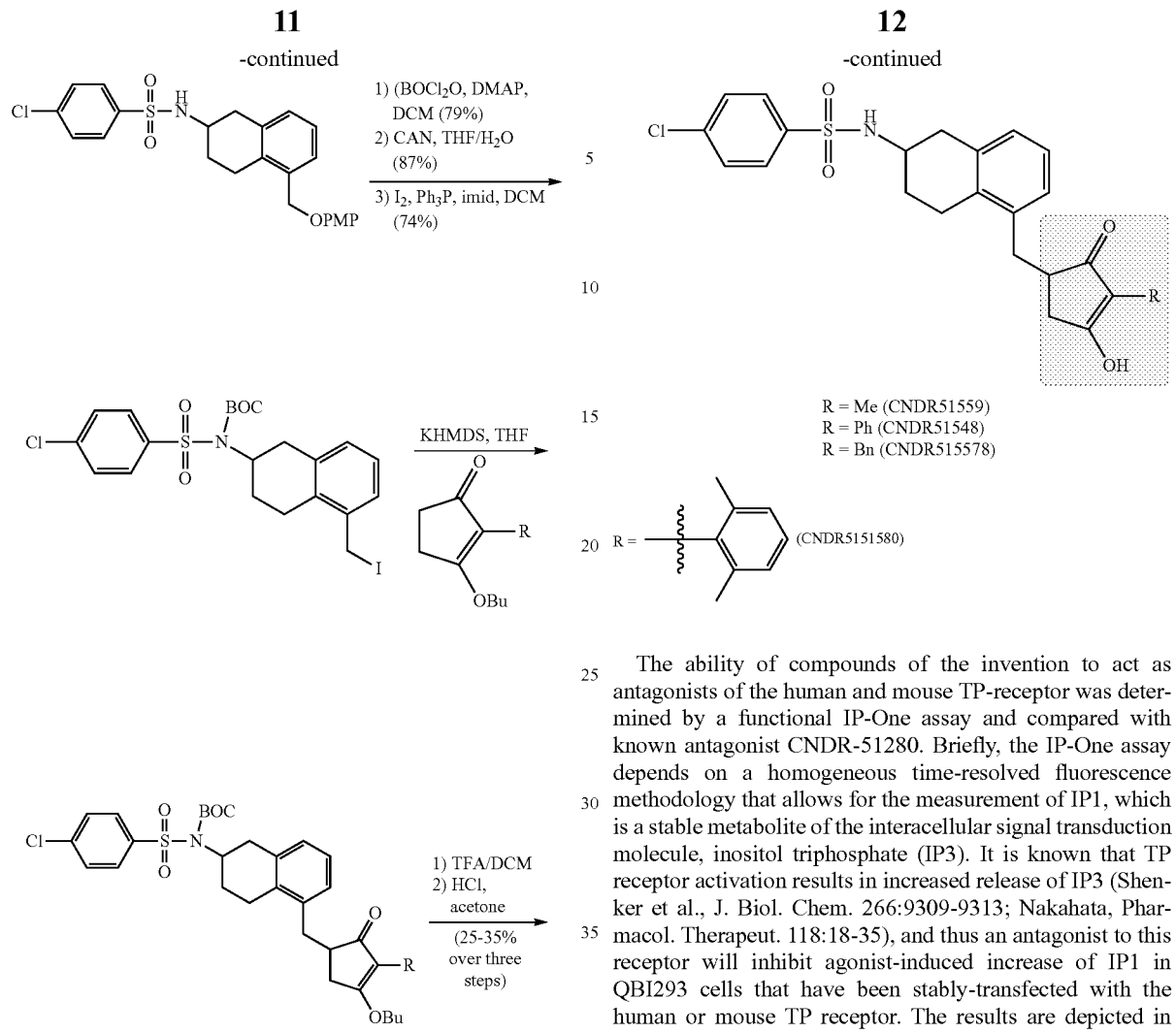

The ability of compounds of the invention to act as antagonists of the human and mouse TP-receptor was determined by a functional IP-One assay and compared with known antagonist CNDR-51280. Briefly, the IP-One assay depends on a homogeneous time-resolved fluorescence methodology that allows for the measurement of IP1, which is a stable metabolite of the interacellular signal transduction molecule, inositol triphosphate (IP3). It is known that TP receptor activation results in increased release of IP3 (Shenker et al., J. Biol. Chem. 266:9309-9313; Nakahata, Pharmacol. Therapeut. 118:18-35), and thus an antagonist to this receptor will inhibit agonist-induced increase of IP1 in QBI293 cells that have been stably-transfected with the human or mouse TP receptor. The results are depicted in Table 1.

TABLE 1

| Cpd# | X | Human TP $IC_{50}$ nm | Mouse TP $IC_{50}$ nM |
|---|---|---|---|
| 51280 | —CH$_2$COOH | 15.7 +/− 3.8 | <10 |
| 51559 | (cyclopentenone-methyl) | 11.2 +/− 5.5 | <10 |

TABLE 1-continued

TP Receptor Antagonist Activity
IPOne Assay

[Core structure: 4-chlorophenylsulfonamide linked to tetrahydronaphthalen-2-yl with CH₂–X substituent]

| Cpd# | X | Human TP IC$_{50}$ nm | Mouse TP IC$_{50}$ nM |
|---|---|---|---|
| 51548 | 2-phenyl-3-hydroxy-cyclopent-2-enone (attached at 5-position) | 3.9 +/− 4.9 | <10 |
| 51578 | 2-benzyl-3-hydroxy-cyclopent-2-enone | 29.2 +/− 14.5 | <10 |
| 51580 | 2-(2,6-dimethylphenyl)-3-hydroxy-cyclopent-2-enone | 0.015 +/− 0.060 | <10 |
| 51574 | 2-(4-fluorophenyl)-3-hydroxy-cyclopent-2-enone | 6.5 +/− 2.6 | <10 |
| 51575 | 2-(4-methoxyphenyl)-3-hydroxy-cyclopent-2-enone | 0.052 +/− 0.88 | <10 |
| 51579 | 2-(2,6-dimethylphenyl)-3-isobutoxy-cyclopent-2-enone | 2760 +/− 1506 | |

As those skilled in the art understand, TP-receptor antagonists are useful in treating disease. Ramatroban, a thromboxane A2 receptor antagonist, is marketed in Japan for the treatment of allergic rhinitis. See, e.g., Suzuki, Y., et al., Prophylactic effects of the histamine H1 receptor antagonist epinastine and the dual thromboxane A2 receptor and chemoattractant receptor-homologous molecule expressed on the Th2 cells antagonist Ramatroban on allergic rhinitis model in mice, Biol. Pharm. Bull. 2011; 34(4); 507-10. TP-receptor antagonists have also been reported for the treatment of diabetic complications, including nephropathy (Xu, S. et al., The thromboxane receptor antagonist S18886 attenuates renal oxidant stress and proteinuria in diabetic apolipoprotein E-deficient mice, Diabetes, 2006 January; 55(1):110-9), and bronchial asthma (Dogne J. M., et al. Thromboxane A2 inhibition: therapeutic potential in bronchial asthma, Am. J. Respir. Med. 2002; 1(1):11-17).

Experimental Section

Those of skill in the art will readily understand that the following procedures are illustrative only, and are not intended to limit the scope of the invention.

Materials and Methods:

All solvents were reagent grade. All reagents were purchased from Aldrich or Acros and used as received. Thin layer chromatography (TLC) was performed with 0.25 mm E. Merck pre-coated silica gel plates. Flash chromatography was performed with silica gel 60 (particle size 0.040-0.062 mm) supplied by Silicycle and Sorbent Technologies. Spots were detected by viewing under a UV light. Yields refer to chromatographically and spectroscopically pure compounds. Infrared spectra were recorded on a Jasco Model FT/IR-480 Plus spectrometer. All melting points were obtained on a Thomas-Hoover apparatus. Proton ($^1$H) and carbon ($^{13}$C) NMR spectra were recorded on a Bruker AMX-500 spectrometer. Chemical shifts were reported relative to solvents (CDCl$_3$ 7.27 ppm; CD$_3$OD 3.35 ppm; DMSO-d$_6$ 2.5 ppm; acetone-d$_6$ 2.05 ppm). High-resolution mass spectra were measured at the University of Pennsylvania Mass Spectrometry Service on either a VG Micromass 70/70H or VG ZAB-E spectrometer. Single-crystal X-ray structure determinations were performed at the University of Pennsylvania with an Enraf Nonius CAD-4 automated diffractometer. Analytical reversed-phased (Sunfire™ C18; 4.6×50 mm, 5 mL) high-performance liquid chromatography (HPLC) was performed with a Water binary gradient module 2525 equipped with Waters 2996 PDA and Water micromass ZQ. All samples were analyzed employing a linear gradient from 10% to 90% of acetonitrile in water over 8 minutes and flow rate of 1 mL/min, and unless otherwise stated, the purity level was >95%. Preparative reverse phase HPLC purification was performed employing Waters SunFire™ prep C$_{18}$ OBD™ columns (5 μm 19×50 or 19×100 mm) All samples were purified employing a linear gradient from 10% to 90% of acetonitrile in water or 15 minutes and flow rate of 20 mL/min. The preparative HPLC system was equipped with Gilson 333 pumps, a 215 Liquid Handler, 845Z injection module, and PDA detector. Unless otherwise stated, all final compounds were found to be >95% pure as determined by HPLC/MS and NMR.

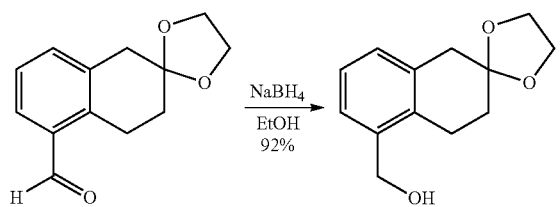

(3',4'-dihydro-1'H-spiro[[1,3]dioxolane-2,2'-naphthalen]-5'-yl)methanol

To a solution of 3',4'-dihydro-1'H-spiro[[1,3]dioxolane-2,2'-naphthalene]-5'-carbaldehyde (652 mg, 2.99 mmol) in EtOH (30 mL) at rt was added NaBH$_4$ (119 mg, 3.15 mmol) in two portions over 20 min. The reaction mixture was stirred at rt for additional 30 min and quenched with saturated NaHCO$_3$ solution (30 mL). The resulting mixture was extracted with CH$_2$Cl$_2$ (3×10 mL). The combined organic layers were dried over Na$_2$SO$_4$, and concentrated. The crude material was purified by column chromatography (2:1 to 3:2 hexanes/EtOAc) to give the product as a white solid (604 mg, 92%). IR (neat, cm$^{-1}$) 3422, 2931, 2885, 1114, 1060; HRMS (ES) m/z (M+Na)$^+$ calcd 243.0997, obsd 243.0999.

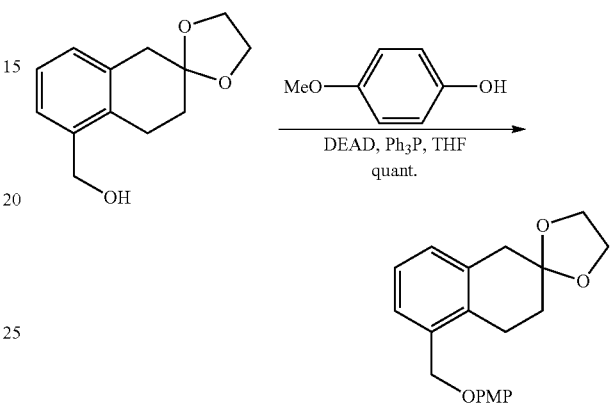

5'-((4-methoxyphenoxy)methyl)-3',4'-dihydro-1'H-spiro[[1,3]dioxolane-2,2'-naphthalene]

To a solution of (3',4'-dihydro-1'H-spiro[[1,3]dioxolane-2,2'-naphthalen]-5'-yl)methanol (1.11 g, 5.04 mmol), 4-methoxyphenol (1.25 g, 10.1 mmol), and Ph$_3$P (2.64 g, 10.1 mmol) in THF (25 mL) at rt was added DEAD (4.6 mL, 40% wt, 10.1 mmol) dropwise. The reaction mixture was stirred at rt for 25 min and quenched with NaHCO$_3$ solution (20 mL). The resulting mixture was diluted with EtOAc (20 mL) and the organic layer was washed successively with 1 M NaOH solution and brine. The organic layer was then dried over Na$_2$SO$_4$ and concentrated. The crude material was purified via column chromatography (4:1 to 3:1 hexanes/EtOAc) to give the product as a colorless oil (1.64 g, quant). IR (neat, cm$^{-1}$) 2931, 1507, 1227; $^1$H NMR (500 MHz, CDCl$_3$) δ 7.31 (br d, J=7.4 Hz, 1H), 7.20 (t, J=7.6 Hz, 1H), 7.09 (br d, J=7.6 Hz, 1H), 6.98-6.95 (m, 2H), 6.90-6.87 (m, 2H), 5.00 (s, 2H), 4.08-4.05 (m, 4H), 3.80 (s, 3H), 3.08 (s, 3H), 3.04 (t, J=6.8 Hz, 2H), 2.04 (t, J=6.8 Hz, 2H); $^{13}$C NMR (125 MHz, CDCl$_3$) δ 153.81, 152.94, 134.98, 134.51, 133.75, 129.41, 126.48, 125.88, 115.56, 114.50, 107.67, 68.94, 64.40, 55.55, 39.26, 31.28, 24.47; HRMS (ES) m/z (M+Na)$^+$ calcd 349.1416, obsd 349.1411.

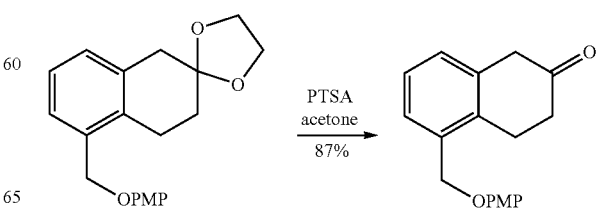

5-((4-methoxyphenoxy)methyl)-3,4-dihydronaphthalen-2(1H)-one

To a solution of 5'-(4-methoxyphenoxy)methyl)-3',4'-dihydro-1'H-spiro[[1,3]dioxolane-2,2'-naphthalene] (142 mg, 0.44 mmol) in acetone (4.3 mL) at rt was added PTSA monohydrate (16.5 mg, 0.088 mmol). The reaction mixture was stirred at rt for 5 h and quenched with water (5.0 mL). The resulting mixture was diluted with EtOAc (10 mL), and the organic layer was separated, dried over $Na_2SO_4$, and concentrated. The crude material was purified via column chromatography (4:1 to 3:1 hexanes/EtOAc) to give the product as a white solid (106 mg, 87%). IR (neat, $cm^{-1}$) 2971, 1715, 1507; $^1$H NMR (500 MHz, $CDCl_3$) δ 7.33 (br d, J=7.5 Hz, 1H), 7.24 (t, J=7.6 Hz, 1H), 7.13 (br d, J=7.5 Hz, 1H), 6.95-6.91 (m, 2H), 6.87-6.85 (m, 2H), 5.04 (s, 2H), 3.78 (s, 3H), 3.62 (s, 3H), 3.13 (t, J=6.6 Hz, 2H), 2.55 (t, J=6.8 Hz, 2H); $^{13}$C NMR (125 MHz, $CDCl_3$) δ 210.30, 154.01, 152.63, 135.99, 134.11, 133.82, 128.58, 127.85, 126.72, 115.64, 114.56, 69.17, 55.57, 45.23, 37.61, 24.12; HRMS (ES) m/z (M+H)$^+$ calcd 283.1334, obsd 283.1346; mp 84-87° C.

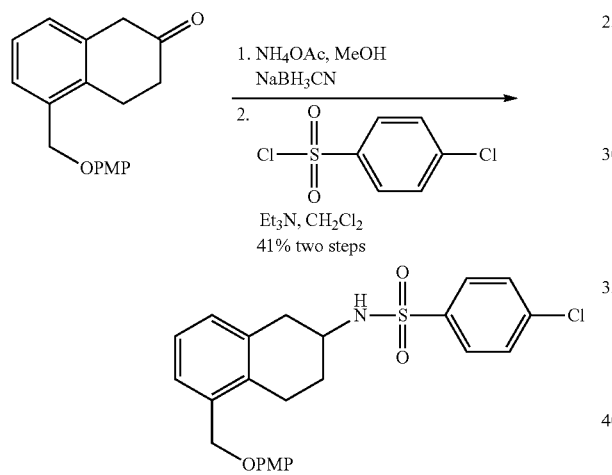

4-chloro-N-(5-((4-methoxyphenoxy)methyl)-1,2,3,4-tetrahydronaphthalen-2-yl)benzene sulfonamide To a solution of 5-((4-methoxyphenoxy)methyl)-3,4-dihydronaphthalen-2(1H)-one (106 mg, 0.38 mmol) and $NH_4OAc$ (290 mg, 3.76 mmol) in MeOH (5.4 mL) at rt was added $NaBH_3CN$ (40 mg, 0.64 mmol) in one portion. The reaction mixture was then stirred at rt overnight and quenched with water (5.0 mL). The resulting mixture was extracted with $CH_2Cl_2$ (3×5.0 mL), and the combined organic layers were dried over $Na_2SO_4$, and then concentrated to give the crude intermediate, which was used directly in the next step.

The crude material from previous step was first dissolved in $CH_2Cl_2$ (5.4 mL) and added $Et_3N$ (0.16 mL, 1.15 mmol). The reaction mixture was then cooled to 0° C., followed by the addition of 4-chlorobenzenesulfonyl chloride (119 mg, 0.56 mmol). The reaction mixture was warmed to rt and stirred for 30 min until completion. The resulting mixture was then quenched with $NaHCO_3$ solution (5.0 mL) and extracted with $CH_2Cl_2$ (3×5.0 mL). The combined organic layers were dried over $Na_2SO_4$ and concentrated. The crude material was purified via column chromatography (4:1 to 3:1 to 2:1 hexanes/EtOAc) to give the product as a yellow solid (70.0 mg, 41% over two steps). $^1$H NMR (500 MHz, $CDCl_3$) δ 7.82 (d, J=8.6 Hz, 2H), 7.46 (d, J=8.6 Hz, 2H), 7.25 (br d, J=7.3 Hz, 1H), 7.12 (t, J=7.6 Hz, 1H), 6.95 (br d, J=7.7 Hz, 1H), 6.92-6.89 (m, 2H), 6.87-6.84 (m, 2H), 5.15 (d, J=7.6 Hz, 1H), 4.89 (s, 2H), 3.78 (s, 3H), 3.68-3.62 (m, 1H), 2.97 (dd, J=16.7, 5.0 Hz, 1H), 2.91-2.84 (m, 1H), 2.81-2.74 (m, 1H), 2.67 (dd, J=16.3, 8.1 Hz, 1H), 2.01-1.94 (m, 1H), 1.80-1.72 (m, 1H); $^{13}$C NMR (125 MHz, $CDCl_3$) δ 153.96, 152.81, 139.47, 138.98, 134.76, 133.72, 133.70, 129.60, 129.36, 128.34, 127.04, 126.06, 115.60, 114.61, 68.98, 55.66, 49.07, 36.67, 29.14, 23.35; HRMS (ES) m/z (M+Na)$^+$ calcd 480.1012, obsd 480.0992; mp 115-120° C.

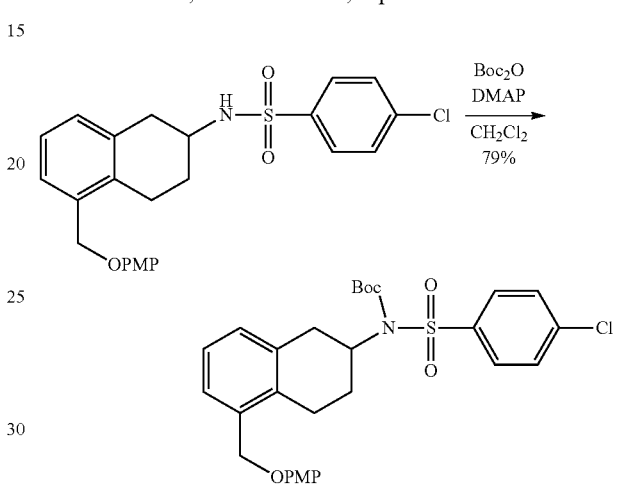

Tert-butyl(4-chlorophenyl)sulfonyl(5-((4-methoxyphenoxy)methyl)-1,2,3,4-tetrahydro-naphthalen-2-yl)carbamate To a solution of 4-chloro-N-(5-(4-methoxyphenoxy)methyl)-1,2,3,4-tetrahydronaphthalen-2-yl)benzenesulfonamide (70.0 mg, 0.15 mmol) in $CH_2Cl_2$ (3.1 mL) at 0° C. was added DMAP (28.0 mg, 0.23 mmol), followed by another solution of $Boc_2O$ (43.4 mg, 0.20 mmol) in $CH_2Cl_2$ (0.7 mL). The reaction mixture was stirred at 0° C. for 40 min and quenched with water (5.0 mL). The resulting mixture was diluted with $CH_2Cl_2$ (10 mL), and the organic layer was separated, dried over $Na_2SO_4$, and concentrated. The crude material was purified via column chromatography (5:1 to 4:1 hexanes/EtOAc) to give the product as a colorless oil (67.5 mg, 79%). IR (neat, $cm^{-1}$) 2931, 1729, 1507, 1363; $^1$H NMR (500 MHz, $CDCl_3$) δ 7.89 (d, J=8.7 Hz, 2H), 7.51 (d, J=8.6 Hz, 2H), 7.28-7.25 (m, 1H), 7.17 (t, J=7.6 Hz, 1H), 7.09 (br d, J=7.6 Hz, 1H), 6.95-6.92 (m, 2H), 6.88-6.85 (m, 2H), 4.96 (s, 2H), 4.81-4.74 (m, 1H), 3.78 (s, 3H), 3.69-3.64 (m, 1H), 3.08-2.99 (m, 2H), 2.97-2.90 (m, 1H), 2.63-2.54 (m, 1H), 2.13-2.08 (m, 1H), 1.40 (s, 9H); $^{13}$C NMR (125 MHz, $CDCl_3$) δ 153.97, 152.92, 150.55, 139.53, 139.29, 135.96, 134.71, 134.12, 129.38, 129.03, 128.99, 126.79, 125.95, 115.66, 114.62, 84.81, 69.16, 55.90, 55.68, 34.13, 27.99, 27.94, 26.69; HRMS (ES) m/z (M+Na)$^+$ calcd 580.1537, obsd 580.1537.

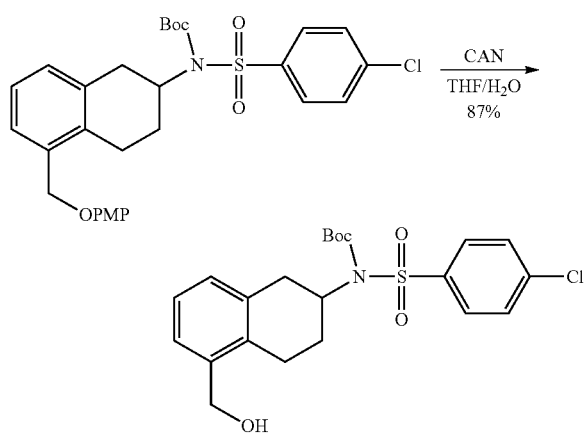

Tert-butyl(4-chlorophenyl)sulfonyl(5-(hydroxymethyl)-1,2,3,4-tetrahydronaphthalen-2-yl)carbamate To a mixture of tert-butyl(4-chlorophenyl)sulfonyl(5-((4-methoxyphenoxy)-methyl)-1,2,3,4-tetrahydronaphthalen-2-yl)carbamate (110 mg, 0.20 mmol) in THF (3.3 mL)/H$_2$O (0.82 mL) at 0° C. was added ceric ammonium nitrate (325 mg, 0.59 mmol) in two portion over 1 h. The reaction mixture was then stirred at 0° C. for 30 min and diluted with EtOAc (10 mL)/H$_2$O (10 mL). The organic layer was separated, dried over Na$_2$SO$_4$, and concentrated. The crude material was purified via column chromatography (2:1 hexanes/EtOAc with 1% EtOH) to give the product as a yellow oil (77.5 mg, 87%). IR (neat, cm$^{-1}$) 3414, 2979, 2932, 1729, 1360; $^1$H NMR (500 MHz, CDCl$_3$) δ 7.87 (d, J=8.6 Hz, 2H), 7.51 (d, J=8.6 Hz, 2H), 7.21 (br d, J=7.3 Hz, 1H), 7.15 (t, J=7.5 Hz, 1H), 7.04 (br d, J=7.6 Hz, 1H), 4.77-4.70 (m, 1H), 4.67 (d, J=4.2 Hz, 2H), 3.66-3.60 (m, 1H), 3.08-3.03 (m, 1H), 3.01-2.97 (m, 1H), 2.92-2.85 (m, 1H), 2.60-2.51 (m, 1H), 2.12-2.07 (m, 1H), 1.38 (s, 9H); $^{13}$C NMR (125 MHz, CDCl$_3$) δ 150.56, 139.55, 139.27, 138.37, 135.86, 133.47, 129.03, 129.00, 128.89, 125.98, 125.45, 84.83, 63.34, 55.95, 34.16, 27.98, 27.93, 26.46; HRMS (ES) m/z (M+Na)$^+$ calcd 474.1118, obsd 474.1116.

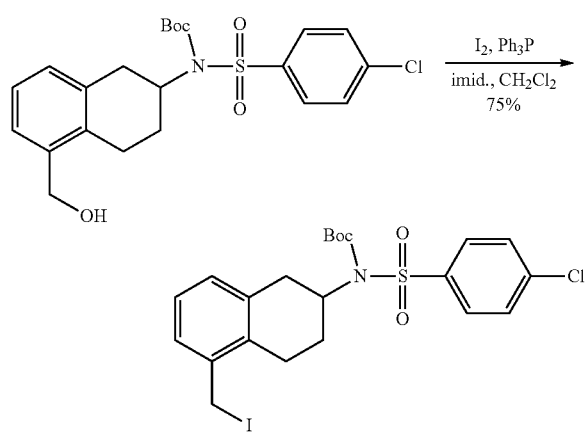

Tert-butyl(4-chlorophenyl)sulfonyl(5-(iodomethyl)-1,2,3,4-tetrahydronaphthalen-2-yl)-carbamate To a solution of tert-butyl(4-chlorophenyl)sulfonyl(5-(hydroxymethyl)-1,2,3,4-tetrahydronaphthalen-2-yl)carbamate (77.5 mg, 0.17 mmol), imidazole (23.3 mg, 0.34 mmol) and Ph$_3$P (67.5 mg, 0.26 mmol) in CH$_2$Cl$_2$ (4.3 mL) at 0° C. was added I$_2$ (65.3 mg, 0.26 mmol) in one portion. The reaction mixture was then warmed to rt, stirred for 2 h, and quenched with water (10 mL). The resulting mixture was diluted with CH$_2$Cl$_2$ (10 mL). The organic layer was separated, dried over Na$_2$SO$_4$, and concentrated. The crude material was purified via column chromatography (8:1 to 6:1 hexanes/EtOAc) to give the product as a white solid (72.3 mg, 75%). $^1$H NMR (500 MHz, CDCl$_3$) δ 7.88 (d, J=8.6 Hz, 2H), 7.52 (d, J=8.6 Hz, 2H), 7.18 (br d, J=7.4 Hz, 1H), 7.09 (t, J=7.6 Hz, 1H), 7.02 (br d, J=7.6 Hz, 1H), 4.79-4.71 (m, 1H), 4.47 (d, J=9.5 Hz, 1H), 4.37 (d, J=9.5 Hz, 1H), 3.65-3.60 (m, 1H), 3.07-2.95 (m, 2H), 2.84-2.77 (m, 1H), 2.66-2.57 (m, 1H), 2.18-2.14 (m, 1H), 1.39 (s, 9H); $^{13}$C NMR (125 MHz, CDCl$_3$) δ 150.55, 139.60, 139.37, 136.65, 136.61, 133.91, 129.57, 129.05, 129.04, 127.48, 126.38, 84.93, 55.80, 34.10, 27.97, 27.77, 26.54, 4.70; HRMS (ES) m/z (M+Na)$^+$ calcd 584.0135, obsd 584.0134; mp decomposed at 180-185° C.

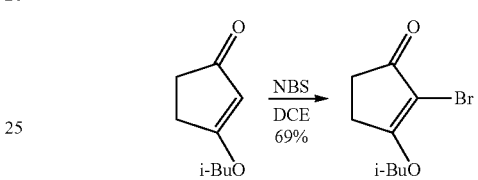

2-Bromo-3-isobutoxycyclopent-2-enone

To a solution of 3-isobutoxycyclopent-2-enone (240 mg, 1.56 mmol) in ClCH$_2$CH$_2$Cl (5.2 mL) at 0° C. was added N-bromosuccinimide (360 mg, 2.02 mmol) in two portions over 30 min. The reaction mixture was stirred at 0° C. for 2 h until completion and quenched with saturated NaHCO$_3$ solution (10 mL). The resulting mixture was diluted with CH$_2$Cl$_2$ (10 mL), and the organic layer was separated, washed with brine, dried over Na$_2$SO$_4$, and concentrated. The crude material was purified via column chromatography (1:1 to 2:3 hexanes/EtOAc) to give the product as a yellow solid (249 mg, 69%).

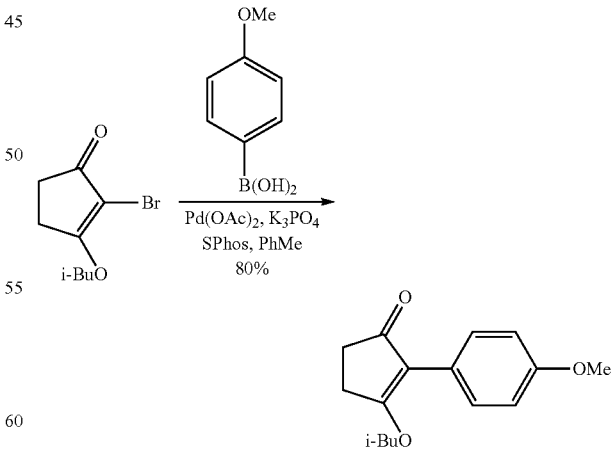

3-Isobutoxy-2-(4-methoxyphenyl)cyclopent-2-enone

A solid mixture of 2-bromo-3-isobutoxy-cyclopent-2-enone (98.7 mg, 0.42 mmol), (4-methoxyphenyl)boronic acid (96.5 mg, 0.64 mmol), SPhos (26.1 mg, 0.064 mmol), K$_3$PO$_4$ (180 mg, 0.85 mmol), and Pd(OAc)$_2$ (4.8 mg, 0.021 mmol) was first purged with N$_2$, and then dissolved in PhMe (1.4 mL). The reaction mixture was degassed with N$_2$ and heated to 90° C. for 90 min. The resulting mixture was diluted with EtOAc (10 mL)/H$_2$O (10 mL) and the organic layer was separated, dried over Na$_2$SO$_4$, and concentrated. The crude material was purified via column chromatography (1:1 to 2:3 hexanes/EtOAc) to give the product as a slightly yellow solid (87.9 mg, 80%). $^1$H NMR (500 MHz, CDCl$_3$) δ 7.74 (d, J=8.8 Hz, 2H), 6.88 (d, J=8.8 Hz, 2H), 3.94 (d, J=6.5 Hz, 2H), 3.77 (s, 3H), 2.72-2.70 (m, 2H), 2.52-2.49 (m, 2H), 2.09-2.01 (m, 1H), 1.00 (d, J=6.7 Hz, 6H); $^{13}$C NMR (125 MHz, CDCl$_3$) δ 203.22, 183.71, 158.08, 129.02, 123.44, 117.44, 113.18, 75.84, 55.00, 33.66, 28.46, 24.75, 18.85.

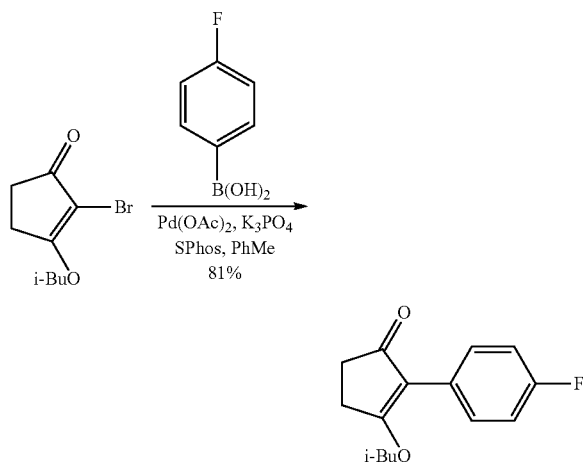

2-(4-fluorophenyl)-3-isobutoxycyclopent-2-enone

A solid mixture of 2-bromo-3-isobutoxy-cyclopent-2-enone (167 mg, 0.72 mmol), (4-fluorophenyl)boronic acid (151 mg, 1.08 mmol), SPhos (44.2 mg, 0.11 mmol), K$_3$PO$_4$ (305 mg, 1.44 mmol), and Pd(OAc)$_2$ (8.1 mg, 0.042 mmol) was first purged with N$_2$, and then dissolved in PhMe (2.4 mL). The reaction mixture was degassed with N$_2$ and heated to 90° C. for 90 min. The resulting mixture was diluted with EtOAc (10 mL)/H$_2$O (10 mL) and the organic layer was separated, dried over Na$_2$SO$_4$, and concentrated. The crude material was purified via column chromatography (1:1 to 2:3 hexanes/EtOAc) to give the product as a slightly yellow solid (145 mg, 81%).

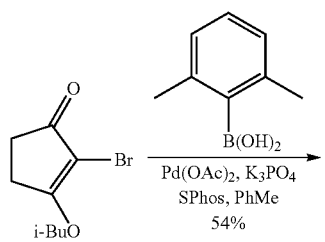

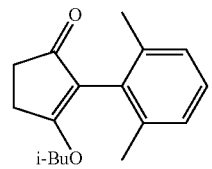

2-(2,6-Dimethylphenyl)-3-isobutoxycyclopent-2-enone

A solid mixture of 2-bromo-3-isobutoxy-cyclopent-2-enone (200 mg, 0.86 mmol), (4-fluorophenyl)boronic acid (193 mg, 1.29 mmol), SPhos (106 mg, 0.26 mmol), K$_3$PO$_4$ (364 mg, 1.71 mmol), and Pd(OAc)$_2$ (19.2 mg, 0.086 mmol) was first purged with N$_2$, and then dissolved in PhMe (2.9 mL). The reaction mixture was degassed with N$_2$ and stirred in a microwave reactor at 120° C. for 40 min, then at 130° C. for 40 min, and finally at 140° C. for 2 h. The resulting mixture was cooled to rt and diluted with EtOAc (10 mL)/H$_2$O (10 mL). The organic layer was separated, dried over Na$_2$SO$_4$, and concentrated. The crude material was purified via column chromatography (1:1 hexanes/EtOAc) to give the product as a colorless oil (120 mg, 54%). IR (neat, cm$^{-1}$) 2961, 1690, 1620, 1353; $^1$H NMR (500 MHz, CDCl$_3$) δ 7.12-7.08 (m, 1H), 7.03-7.01 (m, 2H), 3.67 (d, J=6.5 Hz, 2H), 2.79-2.77 (m, 2H), 2.62-2.59 (m, 2H), 2.12 (s, 6H), 1.89-1.81 (m, 1H), 0.84 (d, J=6.8 Hz, 6H); $^{13}$C NMR (125 MHz, CDCl$_3$) δ 203.70, 183.81, 137.15, 130.70, 127.66, 127.05, 118.87, 76.40, 33.65, 28.44, 26.80, 20.29, 18.68; HRMS (ES) m/z (M+H)$^+$ calcd 259.1698, obsd 259.1698.

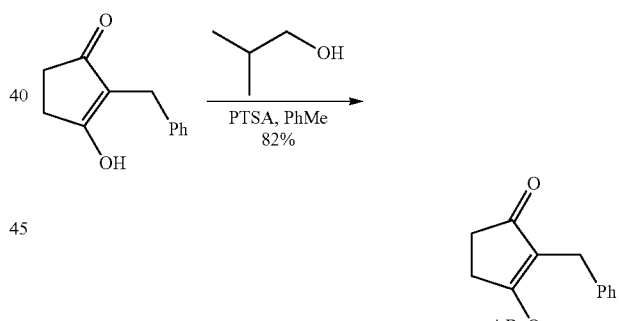

2-Benzyl-3-isobutoxycyclopent-2-enone

A solution of 2-benzyl-3-hydroxycyclopent-2-enone (531 mg, 2.82 mmol) and PTSA monohydrate (26.8 mg, 0.14 mmol) in isobutanol (5.6 mL)/PhMe (9.4 mL) was heated to reflux for 6 h. The reaction mixture was cooled to rt, quenched with saturated NaHCO$_3$ solution (15 mL), and diluted with CH$_2$Cl$_2$ (15 mL). The organic layer was separated, dried over Na$_2$SO$_4$, and concentrated. The crude material was purified via column chromatography (1:1 hexanes/EtOAc) to give the product as a white solid (568 mg, 82%). $^1$H NMR (500 MHz, CDCl$_3$) δ 7.28-7.25 (m, 2H), 7.24-7.20 (m, 2H), 7.16-7.12 (m, 1H), 3.89 (d, J=6.4 Hz, 2H), 3.46 (s, 2H), 2.65-2.62 (m, 2H), 2.46-2.43 (m, 2H), 2.05-1.99 (m, 1H), 0.98 (d, J=6.8 Hz, 6H); $^{13}$C NMR (125 MHz, CDCl$_3$) δ 204.11, 184.74, 140.31, 128.62, 128.16, 125.73, 119.91, 75.49, 33.47, 28.66, 27.35, 24.99, 18.85; HRMS (ES) m/z (M+H)+ calcd 245.1542, obsd 245.1536.

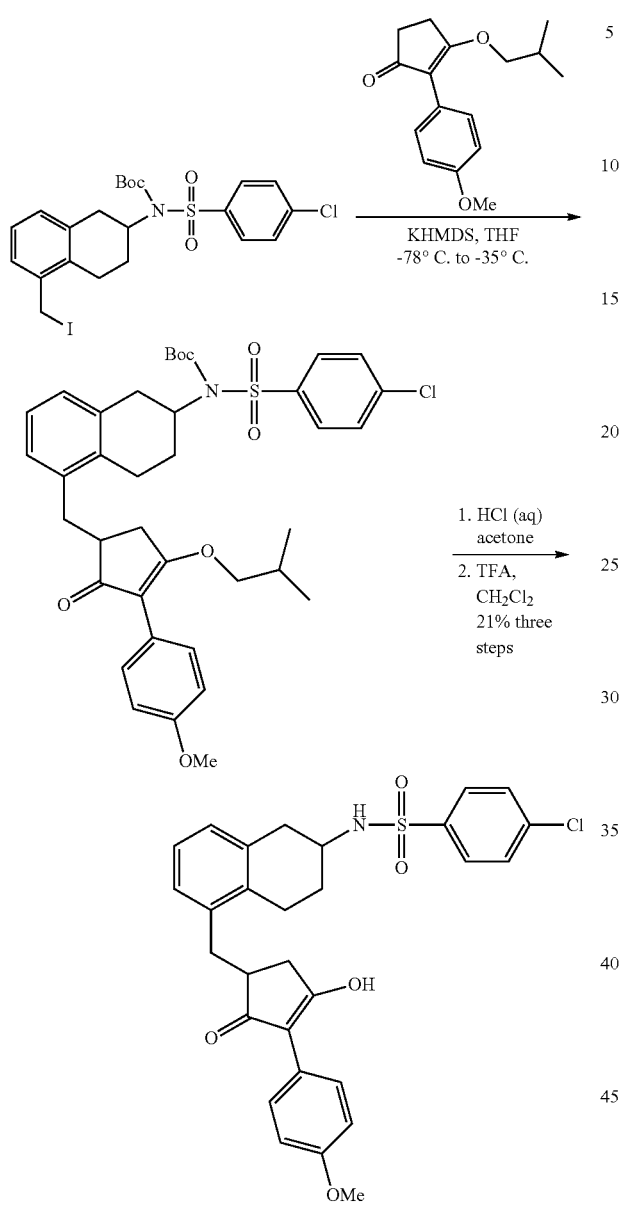

4-Chloro-N-(5-((4-hydroxy-3-(4-methoxyphenyl)-2-oxocyclopent-3-en-1-yl)methyl)-1,2,3,4-tetrahydronaphthalen-2-yl)benzenesulfonamide To a solution of 3-isobutoxy-2-(4-methoxyphenyl)cyclopent-2-enone (28.7 mg, 0.11 mmol) in THF (1.1 mL) at −78° C. was added KHMDS (0.13 mL, 0.5 M in toluene, 0.065 mmol). The resulting mixture was stirred at −78° C. for 35 min and added another solution of tert-butyl(4-chlorophenyl)sulfonyl(5-(iodomethyl)-1,2,3,4-tetrahydronaphthalen-2-yl)carbamate (12.4 mg, 0.022 mmol) in THF (1.1 mL). The resulting mixture was stirred and gradually warmed to −35° C. The reaction was then quenched with H$_2$O (5.0 mL) and diluted with EtOAc (10 mL). The organic layer was separated, washed with brine, dried over Na$_2$SO$_4$, and concentrated. The crude material was purified via column chromatography (2:1 hexanes/EtOAc) to give the intermediate as an orange oil, which was used directly in the next step.

The intermediate from previous step was dissolved in acetone (1.1 mL) and added 2 M HCl(aq) (0.57 mL). The reaction mixture was stirred at 50° C. overnight and concentrated on a rotary evaporator to remove acetone. Water was then removed on a lyophilizer to give a dark orange solid, which was then dissolved in TFA (0.28 mL)/CH$_2$Cl$_2$ (1.1 mL). The resulting mixture was stirred at rt for 1 h until completion and concentrated. The crude material was purified via reverse phase HPLC to give the product as a white solid (2.5 mg, 21% three steps). IR (neat, cm$^{-1}$) 3422, 2928, 1604, 1513; $^1$H NMR (500 MHz, CD$_3$OD) δ 7.89-7.86 (m, 2H), 7.71-7.68 (m, 2H), 7.60-7.56 (m, 2H), 7.01 (br d, J=5.0 Hz, 2H), 6.89 (br d, J=8.4 Hz, 2H), 6.84-6.81 (m, 1H), 3.79 (s, 3H), 3.53-3.47 (m, 1H), 3.28-3.23 (m, 1H), 2.97-2.86 (m, 3H), 2.74-2.64 (m, 2H), 2.63-2.56 (m, 1H), 2.49-2.42 (m, 1H), 2.30-2.24 (m, 1H), 1.98-1.92 (m, 1H), 1.75-1.64 (m, 1H); $^{13}$C NMR (125 MHz, CD$_3$OD) δ 149.28, 142.21, 139.68, 139.13, 139.08, 135.69, 135.64, 134.93, 131.52, 130.43, 130.21, 129.64, 128.63, 128.59, 128.29, 128.16, 126.82, 126.31, 114.94, 114.21, 55.62, 50.86, 50.78, 44.78, 44.50, 38.06, 37.23, 36.25, 35.90, 31.02, 30.92, 25.91, 25.84; HRMS (ES) m/z (M+H)+ calcd 538.1455, obsd 538.1463; mp 135-142° C.

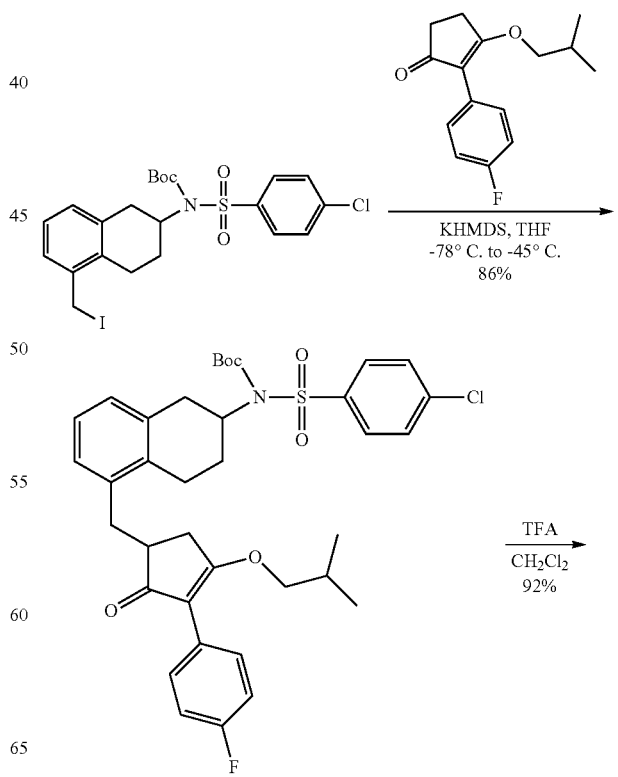

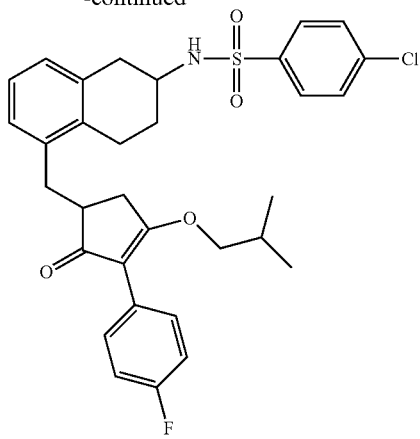

4-Chloro-N-(5-((3-(4-fluorophenyl)-4-isobutoxy-2-oxocyclopent-3-en-1-yl)methyl)-1,2,3,4-tetrahydronaphthalen-2-yl)benzenesulfonamide To a solution of 2-(4-fluorophenyl)-3-isobutoxycyclopent-2-enone (32.1 mg, 0.13 mmol) in THF (1.4 mL) at −78° C. was added KHMDS (0.15 mL, 0.5 M in toluene, 0.075 mmol). The resulting mixture was stirred at −78° C. for 50 min and added another solution of tert-butyl(4-chlorophenyl)sulfonyl(5-(iodomethyl)-1,2,3,4-tetrahydronaphthalen-2-yl)carbamate (24.2 mg, 0.043 mmol) in THF (1.1 mL). The resulting mixture was stirred and gradually warmed to −45° C. The reaction was then quenched with $H_2O$ (5.0 mL) and diluted with EtOAc (10 mL). The organic layer was separated, washed with brine, dried over $Na_2SO_4$, and concentrated. The crude material was purified via column chromatography (3:1 to 2:1 hexanes/EtOAc) to give the intermediate as a slightly yellow oil (25.4 mg, 86%), which was used in the next step.

The intermediate from previous step (25.4 mg, 0.037 mmol) was first dissolved in $CH_2Cl_2$ (2.7 mL), and added TFA (0.66 mL) at 0° C. The reaction mixture was stirred at 0° C. for 3 h until completion and diluted with $H_2O$ (10 mL). The resulting mixture was extracted with $CH_2Cl_2$ (3×10 mL) and the combined organic layers were dried over $Na_2SO_4$, and then concentrated. The crude material was purified via column chromatography (1:1 hexanes/EtOAc) to give the product as a slightly yellow oil (20.0 mg, 92%). IR (neat, cm$^{-1}$) 3263, 2961, 2929, 1681; $^1$H NMR (500 MHz, CDCl$_3$) δ 7.84-7.81 (m, 2H), 7.49-7.47 (m, 2H), 7.44-7.39 (m, 2H), 7.11-7.00 (m, 4H), 6.89-6.86 (m, 1H), 4.92-4.87 (m, 1H), 3.78-3.71 (m, 2H), 3.68-3.61 (m, 1H), 3.28-3.21 (m, 2H), 2.95 (dd, J=16.4, 4.6 Hz, 1H), 2.88-2.78 (m, 1H), 2.76-2.68 (m, 1H), 2.66-2.57 (m, 2H), 2.53-2.47 (m, 1H), 2.30-2.24 (m, 1H), 2.03-1.99 (m, 1H), 1.96-1.88 (m, 1H), 1.85-1.75 (m, 1H), 0.90-0.88 (m, 6H); $^{13}$C NMR (125 MHz, CDCl$_3$) δ 203.51, 185.38, 185.33, 139.55, 139.46, 139.10, 136.89, 133.83, 133.75, 133.31, 133.26, 131.32, 131.30, 131.26, 129.43, 128.42, 128.30, 127.28, 127.10, 126.23, 115.06, 114.89, 78.11, 78.08, 49.08, 48.97, 40.11, 39.95, 38.50, 38.38, 36.90, 36.87, 36.32, 36.23, 29.63, 29.46, 28.71, 24.25, 24.07, 18.75, 18.73; HRMS (ES) m/z (M+H)$^+$ calcd 582.1903, obsd 582.1898.

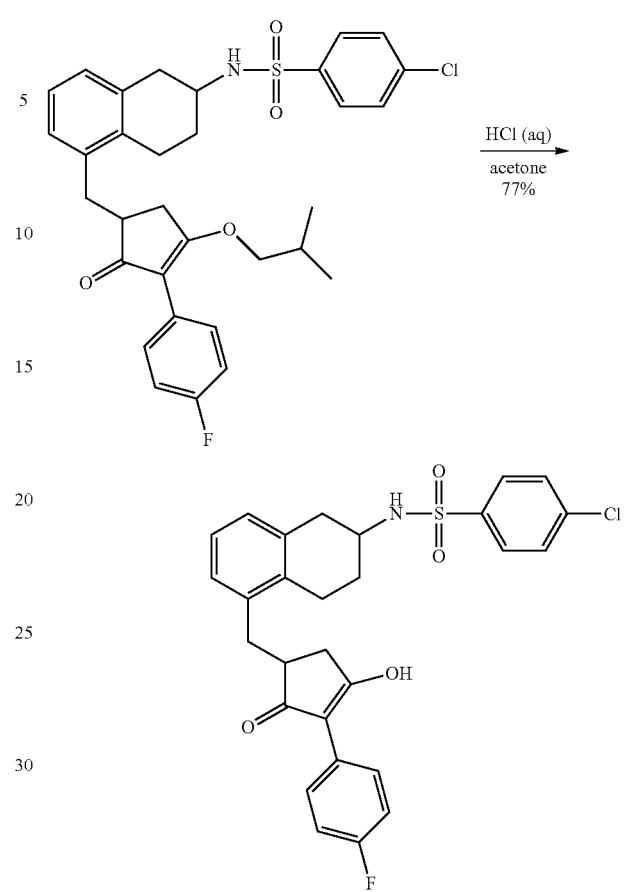

4-Chloro-N-(5-((3-(4-fluorophenyl)-4-hydroxy-2-oxocyclopent-3-en-1-yl)methyl)-1,2,3,4-tetrahydronaphthalen-2-yl)benzenesulfonamide To a solution of 4-chloro-N-(5-((3-(4-fluorophenyl)-4-isobutoxy-2-oxocyclopent-3-en-1-yl)methyl)-1,2,3,4-tetrahydronaphthalen-2-yl)benzenesulfonamide (18.3 mg, 0.031 mmol) in acetone (1.8 mL) at rt was added 2 M HCl(aq) (1.8 mL). The reaction mixture was stirred at rt overnight and added more acetone (1.8 mL). The resulting mixture was then stirred at 40° C. for 4 h and concentrated on a rotary evaporator to remove acetone. The reminder $H_2O$ was then removed on a lyophilizer. The crude material was purified via reverse phase HPLC to give the product as a white solid (12.8 mg, 77%). IR (neat, cm$^{-1}$) 3427, 2925, 1587; $^1$H NMR (500 MHz, CD$_3$OD) δ 7.89-7.86 (m, 2H), 7.83-7.80 (m, 2H), 7.59-7.56 (m, 2H), 7.07-7.01 (m, 4H), 6.84-6.82 (m, 1H), 3.51-3.47 (m, 1H), 3.27-3.23 (m, 1H), 2.95-2.85 (m, 3H), 2.72-2.64 (m, 3H), 2.51-2.45 (m, 1H), 2.36-2.32 (m, 1H), 1.99-1.91 (m, 1H), 1.75-1.64 (m, 1H); $^{13}$C NMR (125 MHz, CD$_3$OD) δ 163.71, 161.77, 142.14, 142.11, 139.67, 138.62, 138.57, 135.83, 135.76, 134.94, 130.89, 130.83, 130.44, 129.64, 128.91, 128.89, 128.85, 128.81, 128.27, 128.07, 126.89, 115.55, 115.38, 50.80, 50.69, 38.01, 37.97, 35.88, 35.50, 31.01, 30.88, 25.89, 25.79; HRMS (ES) m/z (M+H)$^+$ calcd 526.1255, obsd 526.1252; mp 129-133° C.

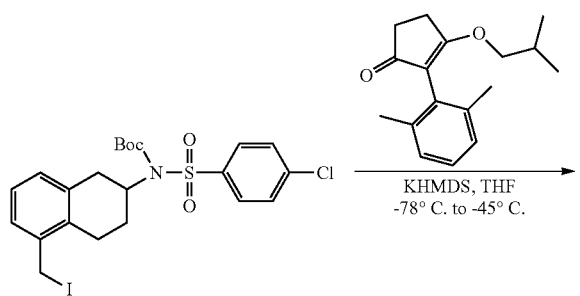

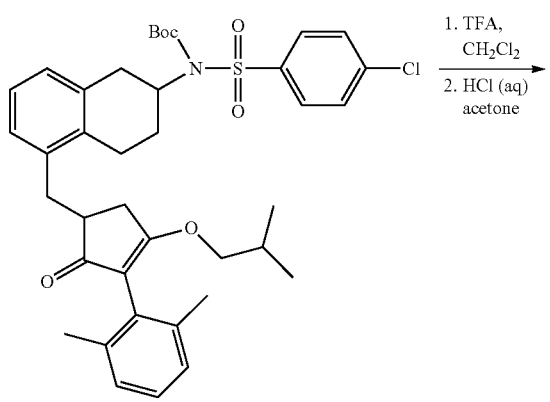

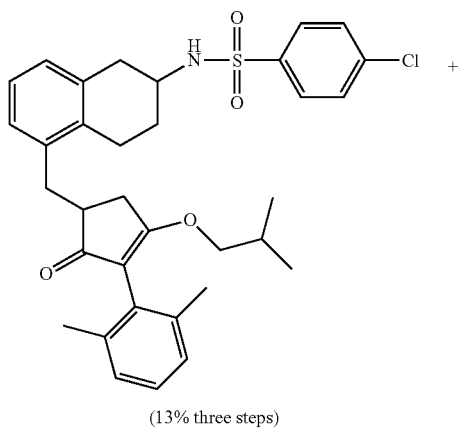

(13% three steps)

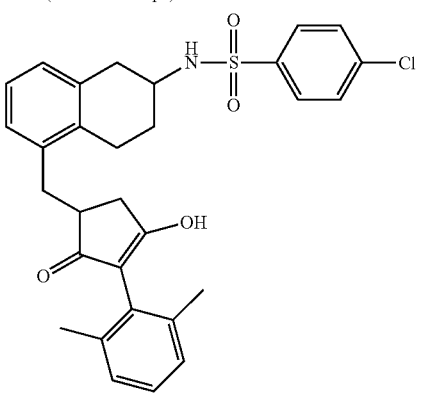

(37% three steps)

4-chloro-N-(5-((3-(2,6-dimethylphenyl)-4-isobutoxy-2-oxocyclopent-3-en-1-yl)methyl)-1,2,3,4-tetrahydronaphthalen-2-yl)benzenesulfonamide and 4-chloro-N-(5-((3-(2,6-dimethyl phenyl)-4-hydroxy-2-oxocyclopent-3-en-1-yl)methyl)-1,2,3,4-tetrahydronaphthalen-2-yl)benzenesulfonamide To a solution of 2-(2,6-dimethylphenyl)-3-isobutoxycyclopent-2-enone (29.0 mg, 0.11 mmol) in THF (1.5 mL) at −78° C. was added KHMDS (0.13 mL, 0.5 M in toluene, 0.065 mmol). The resulting mixture was stirred at −78° C. for 1 h and added another solution of tert-butyl(4-chlorophenyl)sulfonyl(5-(iodomethyl)-1,2,3,4-tetrahydronaphthalen-2-yl)carbamate (21.0 mg, 0.037 mmol) in THF (0.7 mL). The resulting mixture was stirred and gradually warmed to −50° C. The reaction mixture was then quenched with $H_2O$ (5.0 mL) and diluted with EtOAc (10 mL). The organic layer was separated, washed with brine, dried over $Na_2SO_4$, and concentrated. The crude material was then purified via column chromatography (4:1 to 3:1 to 2:1 hexanes/EtOAc) to give the intermediate as a yellow oil, which was used directly in the next step.

The intermediate from previous step was dissolved in $CH_2Cl_2$ (1.8 mL), and added TFA (0.46 mL). The reaction mixture was stirred at rt for 2 h and concentrated. The resulting residue was treated with 2M HCl(aq) (0.70 mL) and acetone (1.4 mL) at 50° C. overnight. Acetone was first removed on the rotary evaporator and water was removed on the lyophilizer. The resulting crude material was then purified via reserve phase HPCL to give the products both as white solids (isobutyl protected product, 2.2 mg, 13% three steps; final deprotected product, 5.5 mg, 37 three steps).

Isobutyl Protected Product:

IR (neat, cm$^{-1}$) 2925, 1679, 1611; $^1$H NMR (500 MHz, CD$_3$OD) δ 7.88 (br d, J=8.5 Hz, 2H), 7.59 (br d, J=8.5 Hz, 2H), 7.16-7.13 (m, 1H), 7.07-7.04 (m, 4H), 6.87-6.85 (m, 1H), 3.52-3.49 (m, 3H), 2.94-2.86 (m, 2H), 2.77-2.55 (m, 4H), 2.32-2.26 (m, 1H), 2.14-2.12 (m, 6H), 1.98-1.93 (m, 1H), 1.79-1.71 (m, 2H), 0.79-0.76 (m, 6H); $^{13}$C NMR (125 MHz, CD$_3$OD) δ 206.96, 188.01, 142.14, 139.68, 138.81, 138.67, 138.36, 135.90, 134.80, 132.58, 130.45, 129.67, 129.23, 129.04, 128.53, 128.23, 128.19, 127.04, 118.51, 78.68, 50.67, 41.61, 40.71, 37.89, 37.11, 30.90, 29.71, 25.87, 20.83, 20.66, 18.92, 18.90; HRMS (ES) m/z (M+H)$^+$ calcd 592.2288, obsd 592.2284.

Final Deprotected Product:

IR (neat, cm$^{-1}$) 3282, 2921, 1584; $^1$H NMR (500 MHz, CD$_3$OD) δ 7.87 (br d, J=8.2 Hz, 2H), 7.58 (br d, J=8.2 Hz, 2H), 7.11-7.02 (m, 5H), 6.84 (br d, J=7.1 Hz, 1H), 3.53-3.46 (m, 1H), 3.30-3.24 (m, 1H), 3.05-3.00 (m, 1H), 2.96-2.85 (m, 2H), 2.76-2.64 (m, 3H), 2.59-2.51 (m, 1H), 1.37-1.31 (m, 1H), 2.16-2.07 (m, 6H), 1.99-1.92 (m, 1H), 1.77-1.69 (m, 1H); $^{13}$C NMR (125 MHz, CD$_3$OD) δ 142.16, 142.11, 139.67, 139.16, 139.05, 138.76, 138.68, 135.79, 135.75, 134.92, 131.36, 130.44, 129.65, 128.79, 128.61, 128.42, 128.32, 128.15, 126.91, 118.06, 117.99, 79.55, 79.29, 79.03, 50.78, 50.70, 44.59, 44.37, 38.00, 37.08, 36.18, 35.71, 30.99, 30.90, 25.90, 25.85, 20.40, 20.32; HRMS (ES) m/z (M+H)$^+$ calcd 536.1662, obsd 536.1657; mp decomposed at 240-245° C.

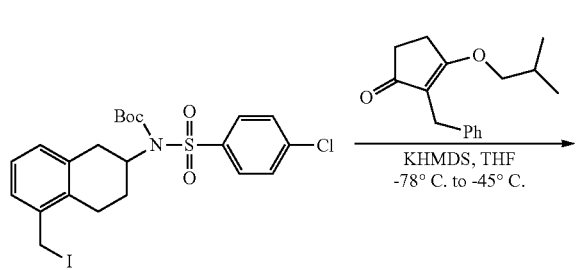

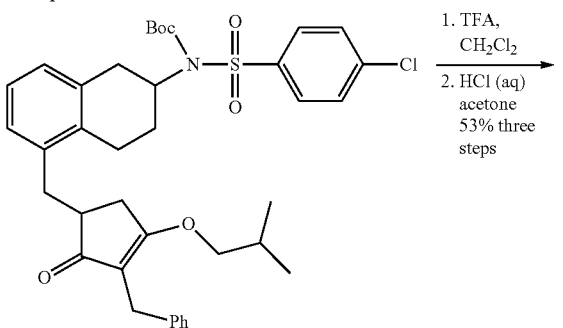

N-(5-((3-benzyl-4-hydroxy-2-oxocyclopent-3-en-1-yl)methyl)-1,2,3,4-tetrahydronaphthalen-2-yl)-4-chlorobenzenesulfonamide To a solution of 2-benzyl-3-isobutoxycyclopent-2-enone (26.0 mg, 0.11 mmol) in THF (1.4 mL) at −78° C. was added KHMDS (0.14 mL, 0.5 M in toluene, 0.070 mmol). The resulting mixture was stirred at −78° C. for 50 min and added another solution of tert-butyl(4-chlorophenyl)sulfonyl(5-(iodomethyl)-1,2,3,4-tetrahydronaphthalen-2-yl)carbamate (19.9 mg, 0.035 mmol) in THF (0.7 mL). The resulting mixture was stirred and gradually warmed to −45° C. The reaction mixture was then quenched with H$_2$O (5.0 mL) and diluted with EtOAc (10 mL). The organic layer was separated, washed with brine, dried over Na$_2$SO$_4$, and concentrated. The crude material was then purified via column chromatography (3:1 to 2:1 to 3:2 hexanes/EtOAc) to give the intermediate as a yellow oil, which was used directly in the next step.

The intermediate from previous step was dissolved in CH$_2$Cl$_2$ (1.8 mL), and added TFA (0.46 mL). The reaction mixture was stirred at rt for 2 h and concentrated. The resulting residue was treated with 2M HCl(aq) (0.70 mL) and acetone (1.4 mL) at 40° C. overnight. Acetone was first removed on the rotary evaporator and water was removed on the lyophilizer. The resulting crude material was then purified via reserve phase HPCL to give the product as a white solid (9.8 mg, 53% three steps). IR (neat, cm$^{-1}$) 3271, 2925, 1584; $^1$H NMR (500 MHz, CD$_3$OD) δ 7.88-7.85 (m, 2H), 7.59-7.56 (m, 2H), 7.20-7.17 (m, 4H), 7.12-7.09 (m, 1H), 6.99-6.94 (m, 2H), 6.81-6.79 (m, 1H), 3.51-3.45 (m, 1H), 3.43 (s, 2H), 3.22-3.15 (m, 1H), 2.91-2.80 (m, 3H), 2.68-2.60 (m, 2H), 2.57-2.49 (m, 1H), 2.44-2.37 (m, 1H), 2.21-2.16 (m, 1H), 1.96-1.88 (m, 1H), 1.72-1.62 (m, 1H); $^{13}$C NMR (125 MHz, CD$_3$OD) δ 142.17, 142.14, 141.75, 141.72, 139.66, 138.75, 138.67, 135.70, 135.64, 134.88, 130.44, 129.64, 129.35, 129.12, 128.71, 128.30, 128.16, 126.84, 126.66, 50.79, 50.69, 44.42, 44.18, 38.01, 36.59, 35.84, 35.38, 30.99, 30.89, 27.67, 25.86, 25.79; HRMS (ES) m/z (M+H)$^+$ calcd 522.1506, obsd 522.1492; mp 145-150° C.

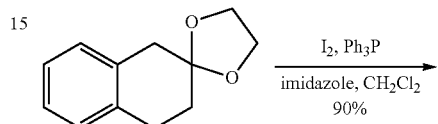

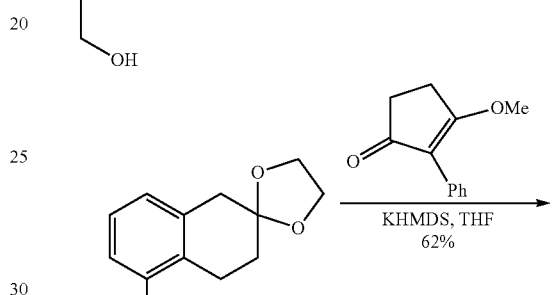

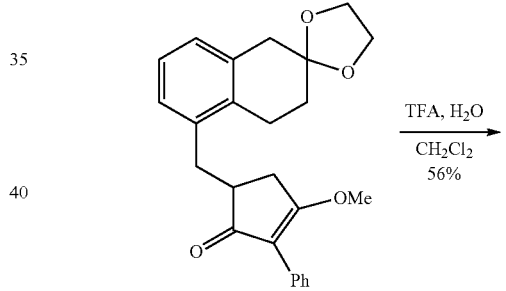

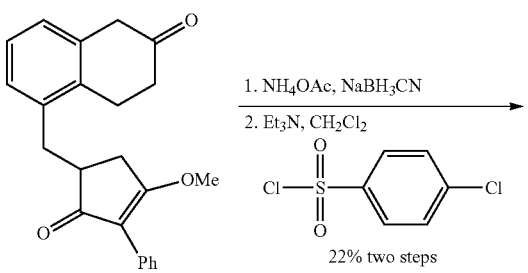

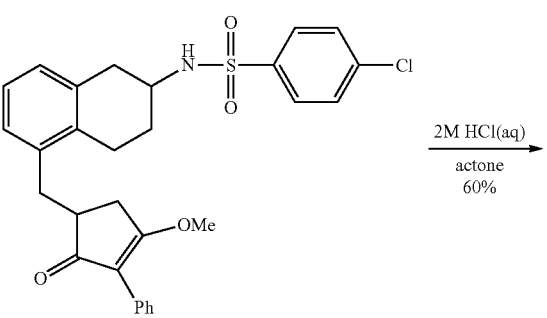

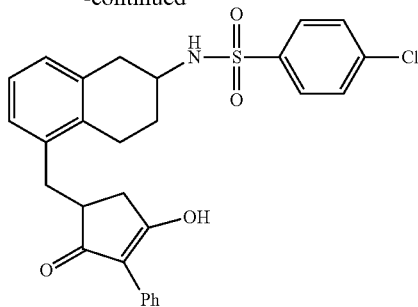

4-Chloro-N-(5-((4-hydroxy-2-oxo-3-phenylcyclopent-3-en-1-yl)methyl)-1,2,3,4-tetrahydro naphthalen-2-yl)benzenesulfonamide To a solution of (3',4'-dihydro-1'H-spiro[[1,3]dioxolane-2,2'-naphthalen]-5'-yl)methanol (31.1 mg, 0.14 mmol), imidazole (19.2 mg, 0.28 mmol), and Ph₃P (55.6 mg, 0.21 mmol) in CH₂Cl₂ (2.8 mL) at 0° C. was added iodine (53.8 mg, 0.21 mmol). The reaction mixture was warmed to rt and stirred for 20 min until completion. The reaction mixture was quenched with saturated NaHCO₃ solution (5.0 mL) and diluted with CH₂Cl₂ (5.0 mL). The organic layer was washed with 10% Na₂S₂O₃ solution, dried over Na₂SO₄, and concentrated. The crude material was then purified by column chromatography (8:1 hexanes/EtOAc) to give the iodide intermediate as a yellow solid (41.9, 90%).

To a solution of 3-methoxy-2-phenylcyclopent-2-enone (71.7 mg, 0.38 mmol) in THF (2.5 mL) at −78° C. was added KHMDS (0.32 mL, 0.5 M in toluene, 0.16 mmol). After stirring for 40 min, a solution of the iodide intermediate from the previous step (41.9 mg, 0.13 mmol) in THF (0.7 mL) was added at −78° C. The reaction mixture was slowly warmed to −25° C. over 2 h. The reaction mixture was quenched with saturated NaHCO₃ solution (5.0 mL), and diluted with EtOAc (5.0 mL). The organic layer was dried over Na₂SO₄, and concentrated. The crude material was then purified by column chromatography (2:1 to 4:3 hexanes/EtOAc) to give the ketal intermediate as a yellow oil (30.9 mg, 62%).

The ketal intermediate from previous step (30.9 mg, 0.079 mmol) was dissolved in CH₂Cl₂/H₂O (2.6 mL/0.13 mL), and added TFA (65.9 µL). The resulting mixture was stirred at rt for 5 h and diluted with CH₂Cl₂/H₂O (5.0 mL/5.0 mL). The organic layer was dried over Na₂SO₄ and concentrated. The crude material was purified by column chromatography (3:2 to 1:1 hexanes/EtOAc) to give the ketone intermediate as a yellow solid (15.3 mg, 56%).

The ketone intermediate from previous step (15.3 mg, 0.044 mmol) was dissolved in MeOH (2.2 mL) and added NH₄OAc (34.0 mg, 0.44 mmol), followed by NaBH₃CN (3.6 mg, 0.057 mmol). The reaction mixture was stirred at rt for 4 h and quenched with saturated NH₄Cl solution (3.0 mL). The resulting mixture was extracted with CH₂Cl₂ (3×3.0 mL). The combined organic layers were dried over Na₂SO₄, and concentrated to give the crude amine, which was used directly in the next step.

The crude amine from previous step was dissolved in CH₂Cl₂ (2.2 mL) at 0° C. and added Et₃N (18.5 µL, 0.13 mmol), followed by the sulfonyl chloride (14.0 mg, 0.066 mmol). The reaction mixture was warmed to rt and stirred for 1 h. The reaction mixture was quenched with saturated NaHCO₃ solution (3.0 mL), and extracted with CH₂Cl₂ (3×3.0 mL). The combined organic layers were dried over Na₂SO₄ and concentrated. The crude material was purified by column chromatography (2:1 hexanes/EtOAc) to give the sulfonamide intermediate as a yellow oil (5.0 mg, 22% two steps).

The sulfonamide intermediate from previous step (5.0 mg, 0.0096 mmol) was dissolved in acetone (0.96 mL) and added 2 M HCl (aq) (0.96 mL). The reaction mixture was stirred at rt overnight and concentrated. The crude material was purified by column chromatography (1:1 hexanes/EtOAc) to give the product as a colorless oil (3.0 mg, 62%). ¹H NMR (500 MHz, CDCl₃) δ 7.82-7.78 (m, 2H), 7.56-7.51 (m, 2H), 7.49-7.45 (m, 2H), 7.43-7.39 (m, 2H), 7.32-7.28 (m, 1H), 7.08-7.01 (m, 2H), 6.88-6.84 (m, 1H), 4.79 (t, J=8.4 Hz, 1H), 3.69-3.62 (m, 1H), 3.30-3.23 (m, 1H), 3.02-2.76 (m, 3H), 2.74-2.68 (m, 1H), 2.67-2.58 (m, 2H), 2.57-2.50 (m, 1H), 2.38-2.33 (m, 1H), 1.96-1.90 (m, 1H), 1.81-1.76 (m, 1H); ¹³C NMR (125 MHz, CDCl₃) δ 139.45, 139.21, 133.65, 133.51, 133.45, 129.71, 129.67, 129.50, 129.08, 128.42, 128.23, 128.04, 127.81, 127.26, 126.24, 53.42, 49.00, 37.01, 36.98, 33.35, 31.92, 29.70, 29.36, 29.32, 24.73, 23.89, 22.69, 14.13, 1.02; HRMS (ES) m/z (M+H)⁺ calcd 508.1349, obsd 508.1341.

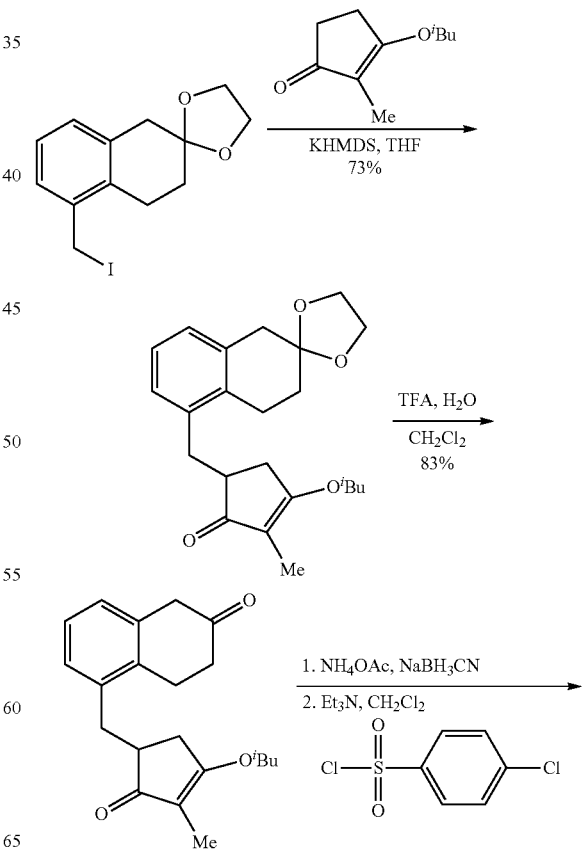

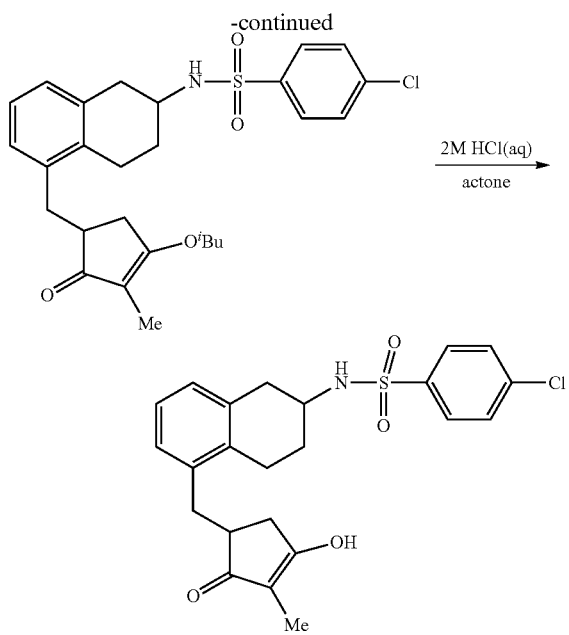

4-Chloro-N-(5-((4-hydroxy-3-methyl-2-oxocyclopent-3-en-1-yl)methyl)-1,2,3,4-tetrahydro naphthalen-2-yl)benzenesulfonamide To a solution of 3-isobutoxy-2-methylcyclopent-2-enone (69.2 mg, 0.41 mmol) in THF (3.3 mL) at −78° C. was added KHMDS (0.45 mL, 0.5 M in toluene, 0.23 mmol). After stirring for 50 min, a solution of 5'-(iodomethyl)-3',4'-dihydro-1'H-spiro[[1,3]dioxolane-2,2'-naphthalene] (56.6 mg, 0.17 mmol) in THF (1.0 mL) was added at −78° C. The reaction mixture was slowly warmed to −15° C. over 2 h. The reaction mixture was quenched with saturated NaHCO$_3$ solution (5.0 mL), and diluted with EtOAc (5.0 mL). The organic layer was dried over Na$_2$SO$_4$, and concentrated. The crude material was then purified by column chromatography (3:2 to 4:3 hexanes/EtOAc) to give the ketal intermediate as a yellow oil (46.1 mg, 73%).

The ketal intermediate from previous step (30.9 mg, 0.079 mmol) was dissolved in CH$_2$Cl$_2$/H$_2$O (2.6 mL/0.13 mL), and added TFA (65.9 µL). The resulting mixture was stirred at rt for 5 h and diluted with CH$_2$Cl$_2$/H$_2$O (5.0 mL/5.0 mL). The organic layer was dried over Na$_2$SO$_4$ and concentrated. The crude material was purified by column chromatography (3:2 to 1:1 hexanes/EtOAc) to give the ketone intermediate as a yellow solid (15.3 mg, 56%).

The ketone intermediate from previous step (15.3 mg, 0.044 mmol) was dissolved in MeOH (2.2 mL) and added NH$_4$OAc (34.0 mg, 0.44 mmol), followed by NaBH$_3$CN (3.6 mg, 0.057 mmol). The reaction mixture was stirred at rt for 4 h and quenched with saturated NH$_4$Cl solution (3.0 mL). The resulting mixture was extracted with CH$_2$Cl$_2$ (3×3.0 mL). The combined organic layers were dried over Na$_2$SO$_4$, and concentrated to give the crude amine, which was used directly in the next step.

The crude amine from previous step was dissolved in CH$_2$Cl$_2$ (2.2 mL) at 0° C. and added Et$_3$N (18.5 µL, 0.13 mmol), followed by the sulfonyl chloride (14.0 mg, 0.066 mmol). The reaction mixture was warmed to rt and stirred for 1 h. The reaction mixture was quenched with saturated NaHCO$_3$ solution (3.0 mL), and extracted with CH$_2$Cl$_2$ (3×3.0 mL). The combined organic layers were dried over Na$_2$SO$_4$ and concentrated. The crude material was purified by column chromatography (2:1 hexanes/EtOAc) to give the sulfonamide intermediate as a yellow oil (5.0 mg, 22% two steps).

The sulfonamide intermediate from previous step (5.0 mg, 0.0096 mmol) was dissolved in acetone (0.96 mL) and added 2 M HCl (aq) (0.96 mL). The reaction mixture was stirred at rt overnight and concentrated. The crude material was purified by column chromatography (1:1 hexanes/EtOAc) to give the product as a colorless oil (3.0 mg, 62%). $^1$H NMR (500 MHz, CD$_3$OD) δ 7.89-7.85 (m, 2H), 7.60-7.56 (m, 2H), 7.02-6.96 (m, 2H), 6.84-6.80 (m, 1H), 4.62 (br s, 1H), 3.52-3.44 (m, 1H), 3.24-3.16 (m, 1H), 2.93-2.79 (m, 3H), 2.71-2.63 (m, 2H), 2.51-2.42 (m, 1H), 2.37-2.31 (m, 1H), 2.17-2.11 (m, 1H), 1.98-1.91 (m, 1H), 1.74-1.65 (m, 1H), 1.58 (s, 3H); $^{13}$C NMR (125 MHz, CD$_3$OD) δ 142.17, 142.16, 139.67, 138.96, 138.92, 135.70, 135.64, 134.86, 134.84, 130.44, 130.32, 129.90, 129.65, 128.68, 128.65, 128.19, 128.01, 126.83, 122.05, 119.86, 112.89, 112.85, 50.80, 50.71, 44.13, 43.87, 38.00, 37.97, 36.92, 36.82, 36.10, 35.73, 31.01, 30.89, 25.86, 25.76, 5.76; HRMS (ES) m/z (M+H)$^+$ calcd 446.1193, obsd 446.1202.

IP1 Functional Assay

Functional activity of the TP receptor was measured by homogenous time-resolved fluorescence (HTRF) (IP-One Tb, Cisbio, Bedford, Mass., USA). QBI-HEK 293A (MP Biomedicals, Solon, Ohio, USA) cells were transfected with human TP receptor or mouse TP receptor cDNAs cloned into the pcDNA5/TO vector (Invitrogen, Carlsbad, Calif., USA), and stable transformants were selected. Cells were plated at 200,000 cells/mL in DMEM containing 4.5 g/L glucose (Invitrogen, Carlsbad, Calif., USA), 10% fetal bovine serum, L-glutamine, and penicillin/streptomycin into 384-well plates (Grenier Bio-One, Monroe, N.C., USA), followed by incubation for 16 hours at 37° C. with 5% CO$_2$.

Culture media was removed and cells were then incubated for 15 min at 37° C. with 5% CO$_2$ in 10 mM Hepes, 1 mM CaCl$_2$, 0.4 mM MgCl$_2$, 4.2 mM KCl, 146 mM NaCl, 5.5 mM glucose, 50 mM LiCl, pH 7.4 (stimulation buffer) containing varying concentrations of test antagonist. I-BOP ([1S-[1α,2α(Z),3β(1E,3S*),4α]]-7-[3-[3-hydroxy-4-(4-iodophenoxy)-1-butenyl]-7-oxabicyclo[2.2.1]hept-2-yl]-5-heptenoic acid) (Cayman Chemicals, Ann Arbor, Mich., USA) was added at a final concentration of 0.2 or 0.8 nM in stimulation buffer and incubated for 1 hour at 37° C. with 5% CO$_2$. D2-labeled IP1 and Tb-labeled Anti-IP1 cryptate were then added in lysis buffer and incubated for 1 hour at 25° C. Plates were then read on a Spectramax M5 microplate reader (Molecular Devices, Sunnyvale, Calif., USA). Data are expressed as the ratio of 665 nm/620 nm fluorescence. IC$_{50}$ values were determined with GraphPad Prism software (GraphPad Software Inc., La Jolla, Calif., USA).

Binding Affinity.

To estimate the binding affinity of compounds of the invention, Shild Plot analysis (Soper et al. ACS Chem. Neurosci., 2012, 3(11):928-40) is conducted.

REFERENCES

1. Patani, G. A.; LaVoie, E. J. Bioisosterism: A Rational Approach in Drug Design. *Chem Rev* 1996, 96, 3147-3176.
2. Boothe, J.; Wilkinson, R.; Kushner, S.; Williams, J. Synthesis of Aureomycin Degradation Products. II. *Journal of the American Chemical Society* 1953, 75, 1732-1733.

3. Hiraga, K. Structures of cyclopentanepolyones. *Chemical & pharmaceutical bulletin* 1965, 13, 1300.
4. Katrusiak, A. Structure of 1,3-cyclopentanedione. *Acta Crystallographica Section C: Crystal Structure Communications* 1990, 46, 1289-1293.
5. Katrusiak, A. Structure of 2-methyl-1,3-cyclopentanedione. *Acta Crystallographica Section C: Crystal Structure Communications* 1989, 45, 1897-1899.
6. Dickinson, R. P.; Dack, K. N.; Long, C. J.; Steele, J. Thromboxane modulating agents. 3. 1H-imidazol-1-ylalkyl- and 3-pyridinylalkyl-substituted 3-[2-[(arylsulfonyl)amino]ethyl]benzenepropanoic acid derivatives as dual thromboxane synthase inhibitor/thromboxane receptor antagonists. *J Med Chem* 1997, 40, 3442-52.
7. Koreeda, M.; Liang, Y.; Akagi, H. Easy generation of the dianions of 3-isobutoxycyclopent-2-en-1-ones and their reactions. *Journal of the Chemical Society, Chemical Communications* 1979, 449-450.
8. Ramachary, D. B.; Kishor, M. Direct amino acid-catalyzed cascade biomimetic reductive alkylations: application to the asymmetric synthesis of Hajos-Parrish ketone analogues. *Organic & Biomolecular Chemistry* 2008, 6, 4176-4187.
9. Tilley, J. W.; Danho, W.; Lovey, K.; Wagner, R.; Swistok, J.; Makofske, R.; Michalewsky, J.; Triscari, J.; Nelson, D.; Weatherford, S. Carboxylic acids and tetrazoles as isosteric replacements for sulfate in cholecystokinin analogs. *Journal of Medicinal Chemistry* 1991, 34, 1125-1136.
10. Henry, J. R.; Marcin, L. R.; McIntosh, M. C.; Scola, P. M.; Davis Harris, G.; Weinreb, S. M. Mitsunobu reactions of n-alkyl and n-acyl sulfonamides—an efficient route to protected amines. *Tetrahedron Letters* 1989, 30, 5709-5712.
11. Peters, L.; Fröhlich, R.; Boyd, A. S. F.; Kraft, A. Noncovalent Interactions between Tetrazole and an N,N'-Diethyl-Substituted Benzamidine. *The Journal of Organic Chemistry* 2001, 66, 3291-3298.
12. Tominey, A. F.; Docherty, P. H.; Rosair, G. M.; Quenardelle, R.; Kraft, A. Unusually Weak Binding Interactions in Tetrazole-Amidine Complexes. *Organic Letters* 2006, 8, 1279-1282.
13. Dogne, J.; Hanson, J.; Leval, X.; Pratico, D.; Pace-Asciak, C.; Drion, P.; Pirotte, B.; Ruan, K. From the design to the clinical application of thromboxane modulators. *Current Pharmaceutical Design* 2006, 12, 903-923.
14. Yamamoto, Y.; Kamiya, K.; Terao, S. Modeling of human thromboxane A2 receptor and analysis of the receptor-ligand interaction. *J Med Chem* 1993, 36, 820-5.
15. Suzuki, Y., et al., Prophylactic effects of the histamine H1 receptor antagonist epinastine and the dual thromboxane A2 receptor and chemoattractant receptor-homologous molecule expressed on the Th2 cells antagonist ramatroban on allergic rhinitis model in mice, Biol. Pharm. Bull. 2011; 34(4); 507-10.
16. Xu, S. et al., The thromboxane receptor antagonist S18886 attenuates renal oxidant stress and proteinuria in diabetic apolipoprotein E-deficient mice, Diabetes, 2006 January; 55(1):110-9
17. Dogne J. M., et al. Thromboxane A2 inhibition: therapeutic potential in bronchial asthma, Am. J. Respir. Med. 2002; 1(1):11-17
18. Ballatore, C. et al, Cyclopentane-1,3-dione: a novel isostere for the carboxylic acid functional group. Application to the design of potent thromboxane (A2) receptor antagonists, J. Med. Chem. 2011 Oct. 13:54(19):6969-83

What is claimed:
1.

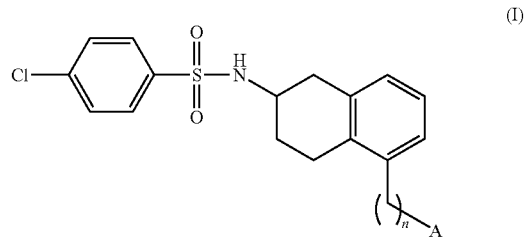

(I)

wherein
A is

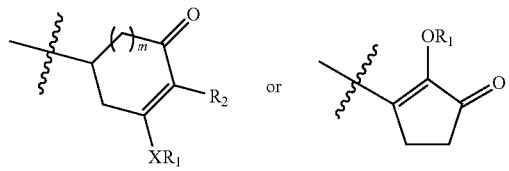

or

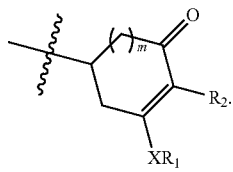

n is 0, 1, or 2;
m is 0 or 1;
$R_1$ is H or $C_{1-6}$alkyl;
$R_2$ is H, $C_{1-6}$alkyl, $C_{1-6}$alkaryl, aryl, or heteroaryl; and
X is O or NH;
or a tautomer, enantiomer, or diastereomer thereof;
or a pharmaceutically acceptable salt form thereof.
2. The compound of claim 1, wherein A is

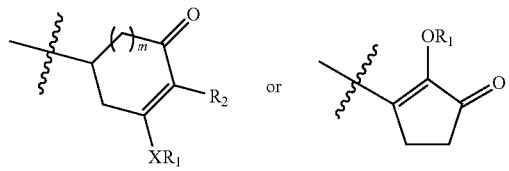

3. The compound of claim 1, wherein m is 0.
4. The compound of claim 1, wherein X is O.
5. The compound of claim 1, wherein n is 1.
6. The compound of claim 1, wherein $R_1$ is H.
7. The compound of claim 1, wherein $R_2$ is $C_{1-6}$alkyl.
8. The compound of claim 7, wherein $R_2$ is methyl, ethyl, propyl, isopropyl, —$CH_2$-cyclopropyl, —$CH_2$-isopropyl, or cyclohexyl.
9. The compound of claim 7, wherein $R_2$ is methyl.
10. The compound of claim 1, wherein $R_2$ is substituted or unsubstituted aryl.
11. The compound of claim 10, wherein $R_2$ is substituted or unsubstituted phenyl.
12. The compound of claim 11, wherein $R_2$ is substituted phenyl.
13. The compound of claim 12, wherein $R_2$ is F-phenyl or methoxyphenyl.
14. The compound of claim 12, wherein $R_2$ is disubstituted phenyl.
15. The compound of claim 14, wherein $R_2$ is di$C_{1-6}$alkyl-substituted phenyl.
16. The compound of claim 15, wherein $R_2$ is dimethylphenyl.

17. The compound of claim 1, wherein the compound is of formula IA

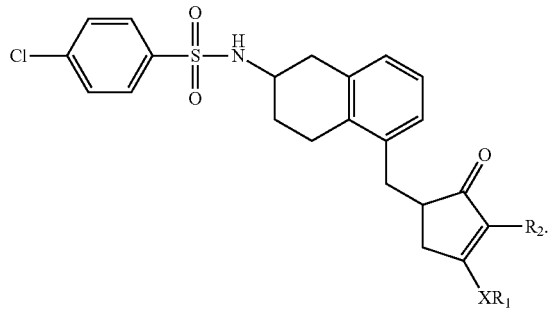

18. The compound of claim 17, wherein $R_1$ is H.
19. The compound of claim 17, wherein $R_1$ is $C_{1-6}$alkyl.
20. The compound of claim 17, wherein X is O; $R_1$ is H; and $R_2$ is $C_{1-6}$alkyl.
21. The compound of claim 20, wherein $R_2$ is methyl, ethyl, propyl, isopropyl, —CH$_2$-isopropyl, or —CH$_2$-cyclopropyl.
22. The compound of claim 17, wherein X is O; $R_1$ is H; and $R_2$ is benzyl.
23. The compound of claim 17, wherein X is O; $R_1$ is H; and $R_2$ substituted or unsubstituted phenyl.
24. The compound of claim 23, wherein $R_2$ is substituted phenyl.
25. The compound of claim 24, wherein $R_2$ is F-phenyl or methoxyphenyl.
26. The compound of claim 24, wherein $R_2$ is disubstituted phenyl.
27. The compound of claim 26, wherein $R_2$ is di$C_{1-6}$alkyl-substituted phenyl.
28. The compound of claim 27, wherein $R_2$ is dimethylphenyl.
29. A pharmaceutical formulation comprising a compound according to claim 1 and a pharmaceutically acceptable carrier or diluent.
30. A method of treating thrombus, Alzheimer's disease, diabetic nephropathy, bronchial asthma, or allergic rhinitis in a patient comprising administering to the patient a compound according to claim 1.

* * * * *